(12) United States Patent
Frank et al.

(10) Patent No.: US 12,216,123 B2
(45) Date of Patent: Feb. 4, 2025

(54) EXTRACELLULAR VESICLE DERIVED MASP-2 DIRECTED CANCER TREATMENT METHODS

(71) Applicant: Nuvance Health, Danbury, CT (US)

(72) Inventors: Richard C. Frank, Fairfield, CT (US); Shatovisha Dey, Danbury, CT (US); Deep Siddhartha Pandya, Stamford, CT (US)

(73) Assignee: Nuvance Health, Danbury, CT (US)

( * ) Notice: Subject to any disclaimer, the term of this patent is extended or adjusted under 35 U.S.C. 154(b) by 0 days.

(21) Appl. No.: 18/650,778

(22) Filed: Apr. 30, 2024

(65) Prior Publication Data

US 2024/0361323 A1  Oct. 31, 2024

Related U.S. Application Data

(63) Continuation of application No. PCT/US2024/025951, filed on Apr. 24, 2024.

(60) Provisional application No. 63/461,833, filed on Apr. 25, 2023.

(51) Int. Cl.
G01N 33/574 (2006.01)

(52) U.S. Cl.
CPC ............. *G01N 33/57438* (2013.01); *G01N 2333/96433* (2013.01)

(58) Field of Classification Search
None
See application file for complete search history.

(56) References Cited

U.S. PATENT DOCUMENTS

| | | | |
|---|---|---|---|
| 10,189,909 B2 | 1/2019 | Larsen et al. | |
| 11,008,404 B2 | 5/2021 | Larsen et al. | |
| 2005/0032157 A1* | 2/2005 | Gal | C12N 9/6424 435/471 |
| 2016/0025734 A1* | 1/2016 | Moses | G01N 33/57434 506/9 |
| 2021/0189009 A1 | 6/2021 | Demopulos et al. | |
| 2022/0026431 A1 | 1/2022 | Delfani et al. | |
| 2023/0075965 A1 | 3/2023 | Mitsiades et al. | |

FOREIGN PATENT DOCUMENTS

| | | | | |
|---|---|---|---|---|
| CN | 109828115 A | * | 5/2019 | |
| WO | WO-2007028795 A1 | * | 3/2007 | ........... C12N 9/6424 |
| WO | 2012151481 A1 | | 11/2012 | |
| WO | WO-2016183176 A1 | * | 11/2016 | ........... A61K 31/522 |
| WO | 2018045054 A1 | | 3/2018 | |
| WO | WO-2020016402 A1 | * | 1/2020 | ....... G01N 33/56905 |
| WO | 2021231720 A1 | | 11/2021 | |

OTHER PUBLICATIONS

Li J, Li Y, Chen S, Duan W, Kong X, Wang Y, Zhou L, Li P, Zhang C, Du L, Wang C. Highly Sensitive Exosome Detection for Early Diagnosis of Pancreatic Cancer Using Immunoassay Based on Hierarchical Surface-Enhanced Raman Scattering Substrate. Small Methods. Jun. 2022;6(6):e2200154. doi: 10.1002/smtd.202200154. Epub Apr. 23, 2022. PMID: 35460217.

Khaled SK, Claes K, Goh YT, Kwong YL, Leung N, Mendrek W, Nakamura R, Sathar J, Ng E, Nangia N, Whitaker S, Rambaldi A; OMS721-TMA-001 Study Group Members. Narsoplimab, a Mannan-Binding Lectin-Associated Serine Protease-2 Inhibitor, for the Treatment of Adult Hematopoietic Stem-Cell Transplantation-Associated Thrombotic Microangiopathy. J Clin Oncol. Aug. 1, 2022;40(22):2447-2457. doi: 10.1200/JCO.21.02389. Epub Apr. 19, 2022. PMID: 35439028; PMCID: PMC9467678.

Lafayette RA, Rovin BH, Reich HN, Tumlin JA, Floege J, Barratt J. Safety, Tolerability and Efficacy of Narsoplimab, a Novel MASP-2 Inhibitor for the Treatment of IgA Nephropathy. Kidney Int Rep. Aug. 13, 2020;5(11):2032-2041. doi: 10.1016/j.ekir.2020.08.003. PMID: 33163724; PMCID: PMC7609886.

International Search Report for International Application No. PCT/US2024/025951, mailed Oct. 1, 2024.

* cited by examiner

*Primary Examiner* — Ellen J Marcsisin
(74) *Attorney, Agent, or Firm* — Wiggin and Dana LLP

(57) ABSTRACT

The present disclosure provides for cancer treatment methods related to the unexpected discovery of the role of mannan-binding protein-associated serine protease-2 (MASP-2) in cancer. Improved cancer treatment methods are disclosed that are determined by measuring changes in levels of MASP-2, a previously unknown biomarker for cancer. It has been discovered that changes in MASP-2 levels are useful as indications of cancer progression, chemotherapeutic responsiveness, and cancer remission, such as in pancreatic cancers. More particularly, changes of levels in MASP-2 in extracellular vesicles (EVs), i.e. EV-MASP2, from patient blood samples are useful for providing effective and targeted cancer treatment regimens, such as in pancreatic cancers. The present disclosure further includes compositions and methods related to inhibiting MASP-2 for the treatment of cancers.

20 Claims, 21 Drawing Sheets

Specification includes a Sequence Listing.

SEQUENCE LISTING

```
Sequence total quantity: 2
SEQ ID NO: 1            moltype = AA  length = 445
FEATURE                 Location/Qualifiers
source                  1..445
                        mol_type = protein
                        organism = Homo sapiens
SEQUENCE: 1
QVTLKESGPV LVKPTETLTL TCTVSGFSLS RGKMGVSWIR QPPGKALEWL AHIFSSDEKS    60
YRTSLKSRLT ISKDTSKNQV VLTMTNMDPV DTATYYCARI RRGGIDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGK                                        445

SEQ ID NO: 2            moltype = AA  length = 212
FEATURE                 Location/Qualifiers
source                  1..212
                        mol_type = protein
                        organism = Homo sapiens
SEQUENCE: 2
QPVLTQPPSL SVSPGQTASI TCSGEKLGDK YAYWYQQKPG QSPVLVMYQD KQRPSGIPER    60
FSGSNSGNTA TLTISGTQAM DEADYYCQAW DSSTAVFGGG TKLTVLGQPK AAPSVTLFPP   120
SSEELQANKA TLVCLISDFY PGAVTVAWKA DSSPVKAGVE TTTPSKQSNN KYAASSYLSL   180
TPEQWKSHRS YSCQVTHEGS TVEKTVAPTE CS                                 212
```

EXTRACELLULAR VESICLE DERIVED MASP-2 DIRECTED CANCER TREATMENT METHODS

CROSS-REFERENCE TO RELATED APPLICATIONS

This application is a continuation of International Application No. PCT/US2024/025951, filed Apr. 24, 2024, which claims priority to U.S. Provisional Patent Application 63/461,833, filed Apr. 25, 2023, each of which are incorporated by reference herein in their entirety.

STATEMENT REGARDING THE SEQUENCE LISTING

The Sequence Listing associated with this application is provided electronically in .xml format and is hereby incorporated by reference into the specification. The Sequence Listing is provided as a file entitled 15558-100501_SL.xml, created Apr. 24, 2024, which is about 4 kB in size.

TECHNICAL FIELD

The present disclosure provides for cancer treatment methods related to the unexpected discovery of the role of mannan-binding protein-associated serine protease-2 (MASP-2) in cancer. Improved cancer treatment methods are disclosed that are determined by measuring changes in levels of MASP-2, a previously unknown biomarker for cancer. It has been discovered that changes in MASP-2 levels are useful as indications of cancer progression, chemotherapeutic responsiveness, and cancer remission, such as in pancreatic cancers. More particularly, changes of levels in MASP-2 in extracellular vesicles (EVs), i.e. EV-MASP2, from patient blood samples are useful for providing effective and targeted cancer treatment regimens, such as in pancreatic cancers. The present disclosure further includes compositions and methods related to inhibiting MASP-2 for the treatment of cancers.

BACKGROUND

Despite major advances in the "war on cancer," leading to improved outcomes for the majority of human malignancies over the past several decades, the mortality rate for some cancers such as pancreatic cancer (PC) has remained stubbornly high. The main reason for this is the high proportion of individuals diagnosed at advanced stages of the disease, coupled with a void in major therapeutic advances other than improved chemotherapeutic regimens. Aside from the 5-7% of PC patients who harbor germline defects in homologous recombination repair genes and who are eligible for "targeted" treatment with a poly (ADP-ribose) polymerase (PARP) inhibitor drug, the genomic and immunotherapy revolutions that have so profoundly impacted multiple cancers have essentially passed by PC. The identification of novel biological targets leading to the development of more effective strategies to treat several incurable cancers, such as pancreatic cancer is therefore, urgently needed.

Pancreatic cancer is presently the $4^{th}$ leading cause of cancer mortality in women and men in the United States. Due to its rising incidence and unchanging, and in many cases unstoppable, lethality, it is projected to become the $2^{nd}$ leading cause of cancer deaths in the United States by 2030. Pancreatic cancer is one of the most difficult to treat human malignancies, with only 10 out of every 100 individuals diagnosed with pancreatic cancer living five years. Most patients are initially diagnosed at an already advanced stage (Stages III or IV) for which overall survival is 10 months on average.

Poor survivals in cancers such as pancreatic cancer are due to the lack of effective early detection strategies, and especially the lack of targeted therapeutic advances. Chemotherapy is the only approved treatment available for advanced stages of pancreatic cancer. Furthermore, oncologists caring for patients with pancreatic cancer, and other high-risk or aggressive cancers, often do not have adequate predictive biomarkers to help guide chemotherapy choices and use. Predictive biomarkers are developed to inform treatment selection by identifying patients who are likely to benefit from a particular therapy. Therefore, both improved ways to treat and improved ways to predict treatment efficacy in pancreatic cancer, and other cancers, are urgently needed.

The present disclosure relates to the surprising discovery that altered levels of mannan-binding protein-associated serine protease-2 (MASP-2; alternatively referred to as mannose-binding protein-associated serine protease-2) at diagnosis and during treatment serves as an effective predictive biomarker for the prognosis and therapeutic response in pancreatic cancer and other cancers. More particularly, serum EV-derived MASP-2 levels (i.e., EV-MASP2 levels) in a patient following initial treatment relative to a before-treatment baseline measurement, are indicative of treatment regimen efficacy. That is, the EV-MASP-2 levels indicate to the physician whether the patient is responding and whether the current regimen should be continued or modified. The present methods based upon EV-MASP-2 levels exhibit high sensitivity and accuracy, and allow for physicians to make early and potentially life-saving treatment regimen decisions before patients progress beyond the point where the cancer is treatable.

A further surprising discovery is that MASP-2 may be targeted for inhibition for the treatment of cancers. The present disclosure therefore further provides for compositions and methods which include the use of a MASP-2 inhibitor for the treatment of cancers, including pancreatic cancer. An MASP-2 inhibitor may be combined with another cancer therapy, such as a chemotherapeutic agent, for improved cancer treatments.

SUMMARY

The present invention generally provides for methods related to the unexpected discovery of the role of mannan-binding protein-associated serine protease-2 (MASP-2) in cancer and related compositions for the treatment of cancer. While the following exemplary embodiments include aspects of the disclosure, these and other embodiments are contemplated herein.

In an embodiment, the present disclosure provides for methods for determining whether to continue or discontinue a first-line cancer therapy in a cancer patient in need thereof, the methods comprising the steps of:
  (a) obtaining a biological sample from the patient prior to or at commencement of a first-line cancer therapy to determine a baseline mannan-binding protein-associated serine protease-2 (MASP-2) level for the patient,
  (b) administering the first-line cancer therapy to the patient according to a treatment regimen over a treatment time period, (c) obtaining a biological sample from the patient during the treatment time period to determine a treatment MASP-2 level, (d) determining whether the treatment MASP-2 level has decreased relative to the baseline MASP-2 level; and (e-i) continuing administering the first-line cancer therapy according to the treatment regimen if the treatment MASP-2 level has decreased (i.e., is not the same or larger) relative to the baseline MASP-2 level, or (e-ii) discontinuing administering the first-line cancer therapy according to the treatment regimen if the treatment MASP-2 level has not decreased (i.e., is the same or larger) relative to the baseline MASP-2 level.

In an embodiment, discontinuing administering the first-line cancer therapy according to the treatment regimen comprises:

(e-ii-a) commencing administering the first-line cancer therapy according to a different treatment regimen;

(e-ii-b) discontinuing administering the first-line cancer therapy and administering no further cancer therapy; and/or (e-ii-c)—commencing administering a second-line cancer therapy according to a treatment regimen.

In an embodiment, the cancer is pancreatic cancer.

In an embodiment, the pancreatic cancer is advanced pancreatic cancer.

In an embodiment, the advanced pancreatic cancer is stage III or stage IV pancreatic cancer.

In an embodiment, the first-line cancer therapy is one or more of chemotherapy, biological therapy, immunotherapy, and hormonal therapy.

In an embodiment, the first-line cancer therapy is FOLFIRINOX, 5-fluorouracil, or gemcitabine alone or in combination with nab-paclitaxel, capecitabine, cisplatin, and/or oxaliplatin.

In an embodiment, the baseline and treatment MASP-2 levels are determined from extracellular vesicles isolated from the biological samples.

In an embodiment, the biological samples are blood samples.

In an embodiment, the baseline and treatment MASP-2 levels are determined from extracellular vesicles isolated from the blood samples.

In an embodiment, the biological sample of step (c) is collected during the treatment time period at a time point from about 2 weeks to about 4 months after commencement of the first-line cancer therapy to determine the treatment MASP-2 level.

In an embodiment, the time point is from about 1 month to about 3 months after commencement of the first-line cancer therapy.

In an embodiment, the time point is about 2 months after commencement of the first-line cancer therapy.

In an embodiment, step (a) comprises the following sub-steps:

(a-i) obtaining a blood sample from the patient prior to or at commencement of a cancer therapy;

(a-ii) isolating extracellular vesicles from the blood sample; and (a-iii) determining, from the isolated extracellular vesicles of step (a-ii), a baseline mannan-binding protein-associated serine protease-2 (MASP-2) level for the patient, and step (c) comprises the following sub-steps (c-i) obtaining a blood sample from the patient during the treatment time period;

(c-ii) isolating extracellular vesicles from the blood sample; and (c-iii) determining, from the isolated extracellular vesicles of step (c-ii), a treatment MASP-2 level.

In an embodiment, the first-line cancer therapy is administered at a first dosage and then, if the MASP-2 level has not decreased relative to the baseline MASP-2 level, the cancer treatment is administered at a second, higher dosage.

In an embodiment, the method comprises:
continuing administering the first-line cancer therapy according to the treatment regimen in step (e-i) or
commencing administering a second-line cancer therapy according to a treatment regimen in step (e-ii)

In an embodiment, the method comprises:
continuing administering the first-line cancer therapy according to the treatment regimen in step (e-i) if the treatment MASP-2 level has a percent decrease from the baseline MASP-2 level greater than or equal to a threshold percent decrease; or (ii) discontinuing the first-line cancer therapy according to the treatment regimen in step (e-ii) if the treatment MASP-2 level has a percent decrease from the baseline MASP-2 level which is less than the threshold percent decrease.

In an embodiment, the threshold percent decrease is a decrease of at least about 10%.

In an embodiment, the threshold percent decrease is a decrease of about 10%.

In an embodiment, a steady or increased MASP-2 level relative to the baseline indicates a risk of further cancer progression.

In an embodiment, a decreased MASP-2 level relative to the baseline indicates a positive response to the treatment regimen.

In an embodiment, the biological sample includes one or more of blood, urine, extracellular vesicles, or whole serum.

In an embodiment, the biological sample is extracellular vesicles.

In an embodiment, the biological sample is whole serum.

In some embodiments, the present disclosure provides for methods for treating cancer in a subject in need thereof comprising administering to the subject an MASP-2 inhibitor.

In an embodiment, the cancer is pancreatic cancer.

In an embodiment, the pancreatic cancer is advanced pancreatic cancer.

In an embodiment, the advanced pancreatic cancer is stage III or stage IV pancreatic cancer.

In an embodiment, the MASP-2 inhibitor is one or more of a small molecule drug, a polypeptide, a polynucleotide, an antibody or antigen-binding fragment thereof, and an siRNA.

In an embodiment, the MASP-2 inhibitor is an antibody or antigen-binding fragment thereof.

In an embodiment, the antibody or antigen-binding fragment thereof comprises one or more of a polypeptide sequence having at least about 80% homology to a sequence according to SEQ ID NO: 1, and a polypeptide sequence having at least about 80% homology to a sequence according to SEQ ID NO: 2.

In an embodiment, the antibody or antigen-binding fragment thereof is the antibody narsoplimab or an antigen-binding fragment thereof.

In an embodiment, the MASP-2 inhibitor is an siRNA.

In an embodiment, the methods further comprise the administration of an additional cancer therapy.

In an embodiment, the additional cancer therapy is a chemotherapy, a biological therapy, an immunotherapy, or a hormonal therapy.

In an embodiment, the additional cancer therapy is one or more chemotherapeutic agents.

In an embodiment, the one or more chemotherapeutic agents are selected from the group consisting of an alkylating agent selected from Altretamine, Bendamustine, Busulfan, Carboplatin, Carmustine, Chlorambucil, Cisplatin, Cyclophosphamide, Dacarbazine, Ifosfamide, Lomustine, Mechlorethamine, Melphalan, Oxaliplatin, Temozolomide, Thiotepa, and/or Trabectedin; a nitrosourea selected from Carmustine, Lomustine, Streptozocin; an antimetabolite selected from Azacitidine, 5-fluorouracil (5-FU), 6-mercaptopurine (6-MP), Capecitabine (Xeloda), Cladribine, Clofarabine, Cytarabine (Ara-C), Decitabine, Floxuridine, Fludarabine, Gemcitabine (Gemzar), Hydroxyurea, Methotrexate, Nelarabine, Pemetrexed (Alimta), Pentostatin, Pralatrexate, Thioguanine, and/or Trifluridine/tipiracil combination; anthracycline or non-anthracycline anti-tumor antibiotics selected from Daunorubicin, Doxorubicin (Adriamycin), Doxorubicin liposomal, Epirubicin, Idarubicin, Valrubicin, Bleomycin, Dactinomycin, Mitomycin-C, Mitoxantrone; topoisomerase I or II inhibitors selected from Irinotecan, Irinotecan liposomal, Topotecan Etoposide (VP-16), Mitoxantrone (also acts as an anti-tumor antibiotic), Teniposide; mitotic inhibitors selected from taxanes, Cabazitaxel, Docetaxel, Nab-paclitaxel, Paclitaxel, vinca alkaloids, Vinblastine, Vincristine, Vincristine liposomal, Vinorelbine; corticosteroids selected from Prednisone, Methylprednisolone, Dexamethasone; and/or other chemotherapy drugs selected from FOLFIRINOX drug combination (fluorouracil (5FU)+ oxaliplatin+ irinotecan+ leucovorin), All-trans-retinoic acid, Arsenic trioxide, Asparaginase, Eribulin, Hydroxyurea, Ixabepilone, Mitotane, Omacetaxine, Pegaspargase, Procarbazine, Romidepsin, and/or Vorinostat.

In an embodiment, the one or more chemotherapeutic agents are selected from the group consisting of: FOLFIRINOX, 5-fluorouracil, and gemcitabine alone or in combination with nab-paclitaxel, capecitabine, cisplatin, and/or oxaliplatin.

In some embodiments, the present disclosure provides for pharmaceutical compositions comprising one or more MASP-2 inhibitors and one or more chemotherapeutic agents.

In an embodiment, the one or more MASP-2 inhibitors include the antibody narsoplimab or an antigen-binding fragment thereof.

In an embodiment, the one or more chemotherapeutic agents include one or more of: an alkylating agent selected from Altretamine, Bendamustine, Busulfan, Carboplatin, Carmustine, Chlorambucil, Cisplatin, Cyclophosphamide, Dacarbazine, Ifosfamide, Lomustine, Mechlorethamine, Melphalan, Oxaliplatin, Temozolomide, Thiotepa, and/or Trabectedin; a nitrosourea selected from Carmustine, Lomustine, Streptozocin; an antimetabolite selected from Azacitidine, 5-fluorouracil (5-FU), 6-mercaptopurine (6-MP), Capecitabine (Xeloda), Cladribine, Clofarabine, Cytarabine (Ara-C), Decitabine, Floxuridine, Fludarabine, Gemcitabine (Gemzar), Hydroxyurea, Methotrexate, Nelarabine, Pemetrexed (Alimta), Pentostatin, Pralatrexate, Thioguanine, and/or Trifluridine/tipiracil combination; anthracycline or non-anthracycline anti-tumor antibiotics selected from Daunorubicin, Doxorubicin (Adriamycin), Doxorubicin liposomal, Epirubicin, Idarubicin, Valrubicin, Bleomycin, Dactinomycin, Mitomycin-C, Mitoxantrone; topoisomerase I or II inhibitors selected from Irinotecan, Irinotecan liposomal, Topotecan Etoposide (VP-16), Mitoxantrone (also acts as an anti-tumor antibiotic), Teniposide; mitotic inhibitors selected from taxanes, Cabazitaxel, Docetaxel, Nab-paclitaxel, Paclitaxel, vinca alkaloids, Vinblastine, Vincristine, Vincristine liposomal, Vinorelbine; corticosteroids selected from Prednisone, Methylprednisolone, Dexamethasone; and/or other chemotherapy drugs selected from FOLFIRINOX drug combination (fluorouracil (5FU)+ oxaliplatin+ irinotecan+ leucovorin), All-trans-retinoic acid, Arsenic trioxide, Asparaginase, Eribulin, Hydroxyurea, Ixabepilone, Mitotane, Omacetaxine, Pegaspargase, Procarbazine, Romidepsin, and/or Vorinostat.

In some embodiments, the present disclosure provides for methods for determining whether to continue or discontinue a first-line cancer therapy in a cancer patient in need thereof, the methods comprising the steps of:
- (a) obtaining a blood sample from the patient prior to or at commencement of a first-line cancer therapy;
- (b) isolating extracellular vesicles from the blood sample and determining, from the isolated extracellular vesicles, a baseline extracellular vesicle-derived mannan-binding protein-associated serine protease-2 (EV-MASP-2) level for the patient,
- (c) administering the first-line cancer therapy to the patient according to a treatment regimen over a treatment time period,
- (d) obtaining a blood sample from the patient during the treatment time period;
- (e) isolating extracellular vesicles from the blood sample obtained during the treatment time period and determining, from the isolated extracellular vesicles, a treatment EV-MASP-2 level;
- (f) determining whether the treatment EV-MASP-2 level has decreased relative to the baseline EV-MASP-2 level; and
- (g-i) continuing administering the first-line cancer therapy according to the treatment regimen if the treatment EV-MASP-2 level has decreased relative to the baseline EV-MASP-2 level, or
- (g-ii) discontinuing administering the first-line cancer therapy according to the treatment regimen if the treatment EV-MASP-2 level has not decreased relative to the baseline EV-MASP-2 level.

In an embodiment, discontinuing administering the first-line cancer therapy according to the treatment regimen comprises:
- (g-ii-a) commencing administering the first-line cancer therapy according to a different treatment regimen; or
- (g-ii-b) discontinuing administering the first-line cancer therapy and administering no further cancer therapy; and/or
- (g-ii-c) commencing administering of second-line cancer therapy according to a treatment regimen.

In an embodiment, the cancer is pancreatic cancer.

In an embodiment, the cancer is advanced pancreatic cancer.

In an embodiment, the advanced pancreatic cancer is stage III or stage IV pancreatic cancer.

In an embodiment, the first-line cancer therapy is one or more of chemotherapy, biological therapy, immunotherapy, and hormonal therapy.

In an embodiment, the first-line cancer therapy is 5-fluorouracil, FOLFIRINOX, or gemcitabine alone or in combination with nab-paclitaxel, capecitabine, cisplatin, and/or oxaliplatin.

In an embodiment, the blood sample of step (d) is collected during the treatment time period at a time point from about 2 weeks to about 4 months after commencement of the first-line cancer therapy to determine the treatment EV-MASP-2 level.

In an embodiment, the time point is from about 1 month to about 3 months after commencement of the first-line cancer therapy.

In an embodiment, the time point is about 2 months after commencement of the first-line cancer therapy.

In an embodiment, the first-line cancer therapy is administered at a first dosage and then, if the EV-MASP-2 level has not decreased relative to the baseline EV-MASP-2 level, the first-line cancer treatment is administered at a higher, second dosage.

In an embodiment, the method comprises:
continuing administering the first-line cancer therapy according to the treatment regimen in step (g-i), or
commencing administering a second-line cancer therapy according to a treatment regimen in step (g-ii).

In an embodiment, the method comprises:
continuing administering the first-line cancer therapy according to the treatment regimen in step (g-i) if the treatment EV-MASP-2 level has a percent decrease from the baseline EV-MASP-2 level greater than or equal to a threshold percent decrease; or
(ii) discontinuing the first-line cancer therapy according to the treatment regimen in step (g-ii) if the treatment EV-MASP-2 level has a percent decrease from the baseline EV-MASP-2 level which is less than the threshold percent decrease.

In an embodiment, the threshold percent decrease is a decrease of at least about 10%.

In an embodiment, the threshold percent decrease is a decrease of 10%.

In an embodiment, a steady or increased EV-MASP-2 level relative to the baseline indicates a risk of further cancer progression.

In an embodiment, a decreased EV-MASP-2 level relative to the baseline indicates a positive response to the treatment regimen.

BRIEF DESCRIPTION OF THE DRAWINGS

Aspects and advantages of the present disclosure will become apparent from the following exemplary embodiments taken in conjunction with the accompanying drawings, of which:

FIGS. 13A and 13B—K-M plots for overall survival analysis in pancreatic cancer patients with CA 19-9 changes. (13A) K-M plot illustrating survival analysis of PC patients evaluated for MASP2, categorized by changes in their CA 19-9 levels. (13B) K-M plot illustrating survival analysis of PC patients in overall study populations categorized by changes in CA 19-9 levels. Comparisons are made for subgroups with a ≥20% rise (blue) versus ≥20% drop in their CA 19-9 levels at month 2 compared to baseline. Median survival times, hazard ratio (HR), and significance from the log-rank test are shown to elucidate the differences in the survival outcomes between the tested groups.

FIG. 15—FIG. 14: K-M plot analyzing overall survival in PC patients with bilirubin >1.3 pre-treatment (n=18), comparing outcomes based on changes in serum EV-MASP2 levels (rise in blue vs. drop in red) at 2 months post-treatment.

DETAILED DESCRIPTION

Figure 1:
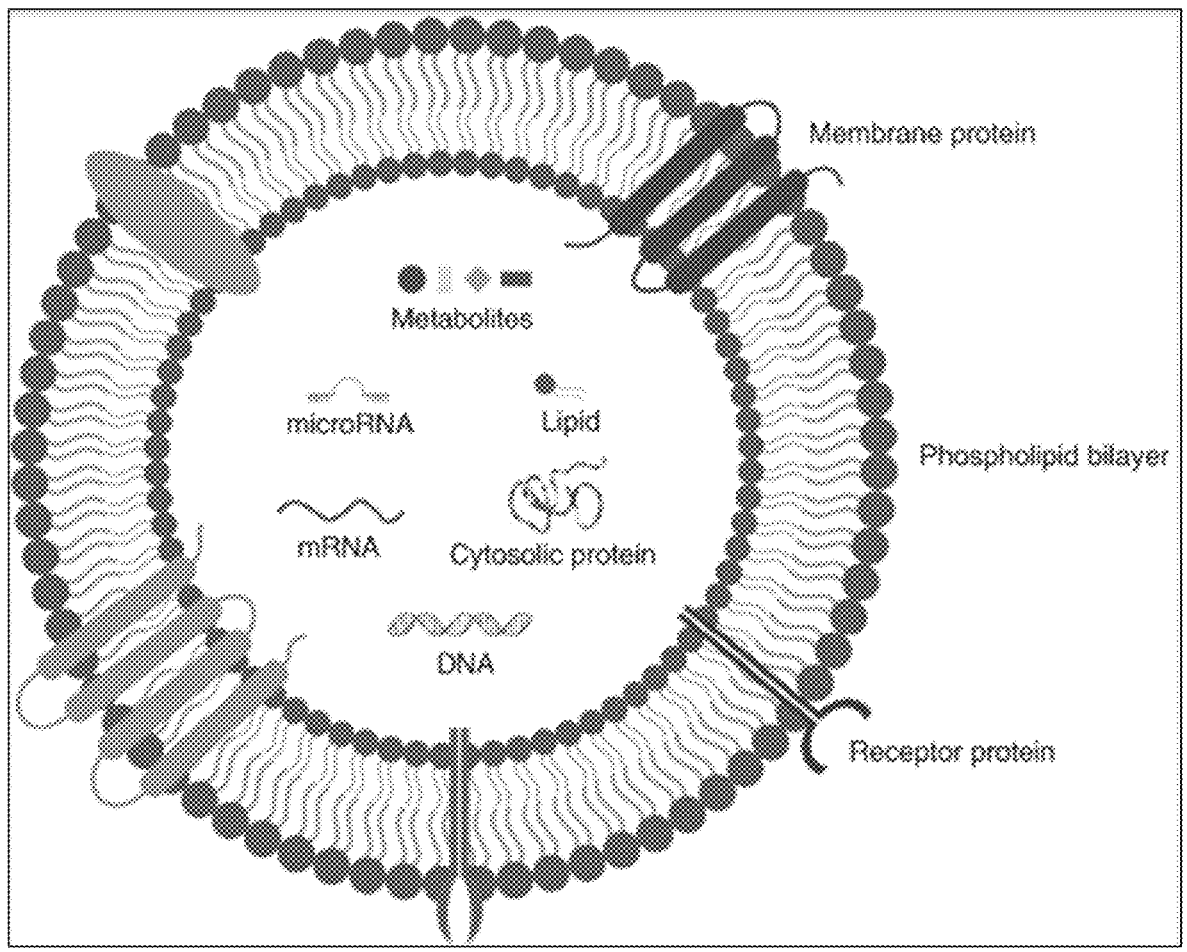
FIG. 1—Diagram of an exemplary extracellular vesicle (EV) structure and biomolecular cargo inside an EV derived from a parent cell.

The present disclosure relates, in some aspects, to the discovery of a new blood-based biomarker of cancer treatment responsiveness. This newly-identified marker, MASP-2, has potential to help oncologists determine if their patients undergoing chemotherapy or other cancer treatment therapies will be responders or non-responders to cancer treatments.

In an embodiment, treatment of cancer in a patient may be directed by changes in the levels of MASP-2 assayed from serum-derived extracellular vesicles of a patient undergoing a cancer treatment regimen. Extracellular vesicles are released into the bloodstream from various cells including cancerous cells. Declining MASP-2 levels during treatment relative to initial levels are indicative of a positive response to the chemotherapy being utilized, whereas rising or stable levels predict a lack of response and the need to change or modify the treatment regimen.

Due to the large number of known cancer treatments and significant unpredictability in treating a particular patient in need thereof with a particular treatment, an individually-tailored treatment method would provide the patient with the best chance of survival. That is, if a physician can make timely adjustments or changes in the treatment regimen in connection with an appropriate efficacy indication (such as a reliable biomarker), there is more opportunity to treat the patient prior to the cancer progressing to an untreatable state. Without such an efficacy indication, the physician may not receive timely enough feedback on treatment progression to know whether or not the treatment is effective. The efficacy indication herein, and the inventive methods involving the same, is the patient MASP-2 level before (i.e. baseline MASP-2 level) and during treatment (i.e. treatment MASP-2 level). If the physician administers an effective treatment, the treatment MASP-2 level will be lowered or decreased relative to the baseline MASP-2 level in accordance with the physician-administered treatment. If no MASP-2 level decrease or a smaller than expected MASP-2 level decrease is observed, thus indicating a lack of efficacy and a lack of response, then the physician will have timely feedback to re-evaluate, change, or modify the treatment regimen.

A patient in need of cancer treatment is therefore subjected to an initial, baseline determination of MASP-2 levels. Preferably, the MASP-2 levels are determined prior to administration of a chemotherapeutic agent or other cancer therapy. Such a pre-treatment measurement would be a "baseline" measurement for making a relative comparison to later in the prescribed treatment regimen. However, if a baseline measurement cannot be, for any reason, taken prior to administration of a chemotherapeutic agent or other cancer therapy, a baseline measurement can alternatively be taken as early as possible in the treatment regimen. Establishing a baseline level of MASP-2 for a given patient is an important step because, depending upon the patient and upon the state of their cancer, MASP-2 levels can vary.

In an alternative embodiment, in the event that a baseline measurement of MASP-2 could not be obtained for any reason, a physician could, instead, compare the patient's MASP-2 levels to an average baseline value for patients having the same or similar cancer, and optionally having the same cancer progression state (i.e. stage). For example, a database of patient baseline MASP-2 levels may be provided. The database may allow the physician to obtain an average MASP-2 baseline level for patients having the same cancer type and same level of progression (i.e. same stage) of the cancer. While a database-provided baseline level is not as preferable as an actual measurement of a patient's baseline MASP-2 levels, it may serve to guide treatment as necessary according to a physician's sound medical judgement. In such cases, the physician can generally rely upon a trend in treatment MASP-2 levels to determine whether or not the first-line cancer therapy is effective, and can evaluate whether an average baseline is an appropriate target.

MASP-2 levels, including the baseline level measurement and any subsequent MASP-2 level measurements obtained during treatment of the cancer, can be determined from any appropriate biological sample from the patient. In some embodiments, the MASP-2 levels are determined from extracellular vesicles present in a patient's blood sample. In other embodiments, MASP-2 levels may be determined from whole serum from a patient's blood sample. In other embodiments, MASP-2 levels may be monitored in other biological samples such as urine.

Extracellular vesicles (EVs) are lipid-bound, heterogeneous populations with a diameter of ~40-160 nm. Under physiological and pathological conditions, almost all cell types secrete EVs into bodily fluids such as blood, saliva, ascites, bile, cerebrospinal fluid and urine. Enriched with varied types of cell-derived bioactive molecules such as DNA, microRNAs (miRNAs), proteins, lipids, and metabolites, EVs carry the signature of the parent cell and maintain cellular homeostasis (FIG. 1). In cancer, tumor derived EVs serve as critical mediators of cellular communication among tumor and neighboring stromal cells in local and distant tumor microenvironment, promoting angiogenesis, immune modulation, stromal remodeling, and metastasis. EVs are obtainable from patient blood draws or liquid biopsies. They carry highly specific contents in an extremely stable state.

EV samples, from which EV-MASP-2 levels may be monitored, may be obtained from the patient from before the beginning of therapy and at one or more timepoints during therapy. In an embodiment, the samples are taken during therapy at timepoints at an interval of once every day, once every two days, once every three days, once every four days, once every five days, once every six days, once every week, bi-weekly (once every other week), once every two weeks, once every three weeks, once every month, once bi-monthly (once every other month), once every third month, or longer. The physician may use sound medical judgement to determine an appropriate sampling interval. In a preferred embodiment, the samples are taken at least monthly (meaning that samples may be taken at a higher frequency than monthly if desirable or necessary).

At each determination of MASP-2 levels during the treatment time period (i.e. the "treatment MASP-2 levels"), a comparison may be made to the baseline MASP-2 level. Generally, if the treatment MASP-2 level has not decreased (i.e. has increased or remained steady), it would be an indication that the cancer therapy or cancer treatment regimen may not be effective or as effective as desired and the physician should change or adjust the cancer therapy or cancer treatment regimen. For example, the physician may change the cancer therapy agent (such as changing to a different chemotherapeutic agent), or may add an additional cancer therapy agent (such as adding an additional chemotherapeutic agent). Additionally or alternatively, the physician my change the cancer treatment regimen by altering the dosage, dosing frequency, etc.

A physician would appreciate that with currently available technologies, there are limited tests and procedures to determine whether or not a patient is a responder to the cancer treatment regimen; this holds especially true for pancreatic cancer. Therefore, the relative comparison of MASP-2 levels during treatment to baseline is a powerful tool to guide treatment. In an embodiment, the patient MASP-2 level may be determined as a ratio of the measured level to the baseline level. The treatment MASP-2 level measured is a result of the specific cancer treatment regimen administered by the physician and is not a natural value or relationship. By monitoring this level, the physician has a highly valuable insight into the treatment efficacy. Even for the same type/stage of cancer, it is possible that different patients will elicit a different treatment response to various treatment regimens. Therefore, various embodiments herein involve monitoring of a treatment-induced condition to inform a physician to make timely and critical life-saving treatment decisions based upon an empirical predictor In various embodiments, MASP-2 levels may be measured from a biological sample. For example, MASP-2 levels may be measured from an extracellular vesicle sample. In an embodiment the extracellular vesicle sample may be derived from a patient's blood serum (i.e., whole serum). In alternative embodiments, MASP-2 levels may be measured from a biological sample other than extracellular vesicles. In an embodiment, the biological sample is a patient blood sample. In an embodiment, the biological sample is a patient blood serum sample. In an embodiment, the biological sample is a urine sample. In alternative embodiments, one or more biological samples may be measured. For example, in an embodiment, both extracellular vesicle and serum samples may be measured. In an alternative embodiment, both extracellular vesicle and urine samples may be measure. In an alternative embodiment, both serum and urine samples may be measured. In such cases, a baseline MASP-2 level would generally be established for each of the one or more biological sample types.

In some embodiments, the cancer is a genitourinary cancer (including but not limited to bladder cancer, kidney cancer, ureteral cancer, any urothelial cancer, testicular cancer, prostate cancer), head/neck cancer, breast cancer, lung carcinoma (including but not limited to the major types squamous, non-squamous/adenocarcinoma, small-cell, neuroendocrine), malignant melanoma, cutaneous squamous cell carcinoma, gynecologic cancers (including but not limited to ovarian, uterine, cervical, primary peritoneal carcinomas, mullerian and, germ-cell tumors), gastrointestinal tract (including but not limited to cancers of the esophagus, stomach, small intestine, large intestine, rectum, anus, liver, bile ducts, pancreas), brain tumors and sarcomas. In particular embodiments, the cancer is pancreatic cancer. In other particular embodiments, the cancer is advanced pancreatic cancer. In further embodiments, the advanced pancreatic cancer is stage III or stage IV pancreatic cancer.

In some embodiments, the chemotherapeutic agent is any known chemotherapeutic agent as determined by a physician using sound medical judgement. In an embodiment, the chemotherapeutic agent is one or more of: an alkylating agent selected from Altretamine, Bendamustine, Busulfan, Carboplatin, Carmustine, Chlorambucil, Cisplatin, Cyclophosphamide, Dacarbazine, Ifosfamide, Lomustine, Mechlorethamine, Melphalan, Oxaliplatin, Temozolomide, Thiotepa, and/or Trabectedin; a nitrosourea selected from Carmustine, Lomustine, Streptozocin; an antimetabolite selected from Azacitidine, 5-fluorouracil (5-FU), 6-mercaptopurine (6-MP), Capecitabine (Xeloda), Cladribine, Clofarabine, Cytarabine (Ara-C), Decitabine, Floxuridine, Fludarabine, Gemcitabine (Gemzar), Hydroxyurea, Methotrexate, Nelarabine, Pemetrexed (Alimta), Pentostatin, Pralatrexate, Thioguanine, and/or Trifluridine/tipiracil combination; anthracycline or non-anthracycline anti-tumor antibiotics selected from Daunorubicin, Doxorubicin (Adriamycin), Doxorubicin liposomal, Epirubicin, Idarubicin, Valrubicin, Bleomycin, Dactinomycin, Mitomycin-C, Mitoxantrone; topoisomerase I or II inhibitors selected from Irinotecan, Irinotecan liposomal, Topotecan Etoposide (VP-16), Mitoxantrone (also acts as an anti-tumor antibiotic), Teniposide; mitotic inhibitors selected from taxanes, Cabazitaxel, Docetaxel, Nab-paclitaxel, Paclitaxel, vinca alkaloids, Vinblastine, Vincristine, Vincristine liposomal, Vinorelbine; corticosteroids selected from Prednisone, Methylprednisolone, Dexamethasone; and/or other chemotherapy drugs selected from FOLFIRINOX drug combination (fluorouracil (5FU)+ oxaliplatin+ irinotecan+ leucovorin), All-trans-retinoic acid, Arsenic trioxide, Asparaginase, Eribulin, Hydroxyurea, Ixabepilone, Mitotane, Omacetaxine, Pegaspargase, Procarbazine, Romidepsin, and/or Vorinostat.

As used herein, the term "cancer therapy" is intended to encompass any known cancer treatment compounds, composition, combination therapies, etc. As such, a "cancer therapy" may include one or more chemotherapeutic agents. A "cancer therapy" may be referred to as "cancer therapy agent" where appropriate grammatically. As described further herein, cancer therapies can include first-line cancer therapies, second-line cancer therapies, third-line cancer therapies, etc. A "cancer therapy" may further include one or more hormone therapy agent(s) (i.e. agents for hormonal therapy most commonly used to treat breast and prostate cancers), and/or one or more immunotherapy agent(s) (i.e. agents for immunotherapy, for example and not limited to those targeting the PD-1/PD-L1 and CTLA4 pathways). In further embodiments, the "cancer therapy" may comprise a targeted therapy, a targeted biologic therapy, or a targeted small drug therapy (where targeted therapies are specific to a protein or receptor expressed or overexpressed in the cancer cells, for example but not limited to therapies targeting the Her-2 protein (trastuzumab, T-DM1, others, or angiogenesis inhibitors that target the tumor vasculature, such as but not limited to bevacizumab, ramucirumab, axitinib, sunitinib, cabozantinib). For example, certain therapies might include antibodies or antigen-binding fragments thereof, monoclonal antibodies, checkpoint inhibitors, inhibitors of proteins overexpressed in cancers, inhibitors related to malignancy or cancer progression, siRNA inhibitors of cancer, CRISPR or other gene editing techniques etc. A physician using sound medical judgement may determine whether or not a particular medicine is a "cancer therapy".

As used herein, the term "regimen" or "treatment regimen" encompasses the time interval and dosage of the "cancer therapy" or in some cases, another active agent (such as an MASP-2 inhibitor). The cancer therapy or active agent may be administered at an interval of once or more every day, once or more every two days, once or more every three days, once or more every four days, once or more every five days, once or more every six days, once or more every week, bi-weekly (once or more every other week), once or more every two weeks, once or more every three weeks, once or more every month, once or more bi-monthly (once or more every other month), once or more every third month, or longer. The physician may use sound medical judgement to determine an appropriate treatment regimen interval. The physician may also use sound medical judgement to determine an appropriate dosage of the cancer therapy or other active agent. By way of example, pancreatic cancer, the following cancer chemotherapy drugs and their standard doses are: 5-fluorouracil @2,400 mg/m2 as an intravenous infusion, 5-fluorouracil @400 mg/m2 as an intravenous push, leucovorin @400 mg/m2 as a 2 hour infusion, oxaliplatin @85 mg/m2 intravenous, irinotecan @150 mg or 185 mg/m2 intravenous, gemcitabine @1000 mg/m2 intravenous, nab-paclitaxel (Abraxane) 125 mg/m2 intravenous, cisplatin 25 mg/m2 intravenous, liposomal irinotecan (Onyvide) 85 mg/m2 intravenous. In various embodiments, these chemotherapy drugs and their standard doses may be prescribed by the physician alone or in combination with an MASP-2 inhibitor as informed by certain changes in MASP-2 levels subsequent to initial chemotherapy treatment(s). A physician may change or adjust the treatment regimen as informed by MASP-2 level measurements.

In a further embodiment, a physician may track a rate of change of an MASP-2 level compared to baseline over two or more samples taken after the treatment regimen has been started. In a further embodiment, the physician may monitor a rate of change to identify increasing or decreasing rates of change, plateaus, or other features. In a further embodiment, the physician may apply further mathematical or statistical transformations to make a determination as to the preferred course of treatment. In a further embodiment, after determining that a patient is responding to the treatment, the physician may continue to monitor the MASP-2 levels to determine whether the treatment needs to be adjusted at some time subsequent to the initial determination that the patient is responding. Using sound medical judgement, the physician may change or adjust the treatment regimen if the MASP-2 levels begin to increase again, or if they increase to some percentage of the baseline.

In addition, it has been discovered that MASP-2 plays a role in chemotherapy sensitivity of pancreatic cancer cells and is a drug target to treat the disease. Methods of administering one or more MASP-2 inhibitors for treating cancer are also provided herein. In an embodiment, the MASP-2 inhibitor is a small molecule drug, an antibody or antigen-binding fragment thereof, an oligonucleotide, an siRNA, CRISPR gene target, or any other MASP-2 inhibitor agent having MASP-2 inhibitory properties. In an embodiment, the cancer targeted by the MASP-2 inhibitor is pancreatic cancer.

In an embodiment, the MASP-2 inhibitor is an antibody or antigen-binding fragment thereof. In an embodiment, the antibody or antigen-binding fragment thereof that binds an epitope within the C-terminal part of MASP-2. In an embodiment, the antibody or antigen-binding fragment thereof binds one or more of the CCP1, CCP2 and serine protease domains of MASP-2. A MASP-2 inhibitor may be the narsoplimab antibody or an antigen-binding fragment thereof. The heavy and light chain polypeptide sequences, respectively SEQ ID No: 1 and SEQ ID No: 2, for narsoplimab are provided in Table 1.

TABLE 1 narsoplimab heavy and light chain polypeptide sequences (Heavy chain)

QVTLKESGPV LVKPTETLTL TCTVSGFSLS RGKMGVSWIR QPPGKALEWL
AHIFSSDEKS
YRTSLKSRLT ISKDTSKNQV VLTMTNMDPV DTATYYCARI RRGGIDYWGQ
GTLVTVSSAS
TKGPSVFPLA PCSRSTSEST AALGCLVKDY FPEPVTVSWN SGALTSGVHT
FPAVLQSSGL
YSLSSVVTVP SSSLGTKTYT CNVDHKPSNT KVDKRVESKY GPPCPPCPAP
EFLGGPSVFL
FPPKPKDTLM ISRTPEVTCV VVDVSQEDPE VQFNWYVDGV EVHNAKTKPR
EEQFNSTYRV
VSVLTVLHQD WLNGKEYKCK VSNKGLPSSI EKTISKAKGQ PREPQVYTLP
PSQEEMTKNQ
VSLTCLVKGF YPSDIAVEWE SNGQPENNYK TTPPVLDSDG SFFLYSRLTV
DKSRWQEGNV
FSCSVMHEAL HNHYTQKSLS LSLGK (SEQ ID NO: 1)

(Light chain)

QPVLTQPPSL SVSPGQTASI TCSGEKLGDK YAYWYQQKPG QSPVLVMYQD
KQRPSGIPER

TABLE 1-continued narsoplimab heavy and light chain polypeptide sequences

```
FSGSNSGNTA TLTISGTQAM DEADYYCQAW DSSTAVFGGG TKLTVLGQPK
AAPSVTLFPP
SSEELQANKA TLVCLISDFY PGAVTVAWKA DSSPVKAGVE TTTPSKQSNN
KYAASSYLSL
TPEQWKSHRS YSCQVTHEGS TVEKTVAPTE CS (SEQ ID NO: 2)
```

In an embodiment, the present disclosure provides methods for treating a cancer by administering to a subject in need thereof an MASP-2 inhibitor comprising a sequence having at least 80% homology with a sequence according to either SEQ ID NO: 1 or SEQ ID NO: 2. In an embodiment, the present disclosure provides methods for treating a cancer by administering to a subject in need thereof an MASP-2 inhibitor comprising a sequence having at least 85%, 90%, 95%, 97%, 98%, 99%, or 100% homology with a sequence according to either SEQ ID NO: 1 or SEQ ID NO: 2. In an embodiment, the present disclosure provides methods for treating pancreatic cancer by administering to a subject in need thereof an MASP-2 inhibitor comprising a sequence having at least 80% homology with a sequence according to either SEQ ID NO: 1 or SEQ ID NO: 2. In an embodiment, the present disclosure provides methods for treating pancreatic cancer by administering to a subject in need thereof an MASP-2 inhibitor comprising a sequence having at least 85%, 90%, 95%, 97%, 98%, 99%, or 100% homology with a sequence according to either SEQ ID NO: 1 or SEQ ID NO: 2.

In an embodiment, the present disclosure provides methods for treating a cancer by administering to a subject in need thereof an MASP-2 inhibitor comprising one or more sequences having at least 80% homology with a sequence according to SEQ ID NO: 1 and one or more sequences having at least 80% homology with a sequence according to SEQ ID NO: 2. In an embodiment, the present disclosure provides methods for treating a cancer by administering to a subject in need thereof an MASP-2 inhibitor comprising one or more sequences having at least 85%, 90%, 95%, 97%, 98%, 99%, or 100% homology with a sequence according to SEQ ID NO: 1 and one or more sequences having at least 85%, 90%, 95%, 97%, 98%, 99%, or 100% homology with a sequence according to SEQ ID NO: 2. In an embodiment, the present disclosure provides methods for treating pancreatic cancer by administering to a subject in need thereof a MASP-2 inhibitor comprising one or more sequences having at least 80% homology with a sequence according to SEQ ID NO: 1 and one or more sequences having at least 80% homology with a sequence according to SEQ ID NO: 2. In an embodiment, the present disclosure provides methods for treating pancreatic cancer by administering to a subject in need thereof an MASP-2 inhibitor comprising one or more sequences having at least 85%, 90%, 95%, 97%, 98%, 99%, or 100% homology with a sequence according to SEQ ID NO: 1 and one or more sequences having at least 85%, 90%, 95%, 97%, 98%, 99%, or 100% homology with a sequence according to SEQ ID NO: 2.

In an embodiment, the present disclosure provides methods for treating a cancer by administering to a subject in need thereof 1) an MASP-2 inhibitor comprising a sequence having at least 80% homology with a sequence according to either SEQ ID NO: 1 or SEQ ID NO: 2; and 2) an additional cancer therapy agent (i.e. chemotherapeutic agent, biologic, immunotherapy, or other cancer-specific therapy). In an embodiment, the present disclosure provides methods for treating a cancer by administering to a subject in need thereof 1) an MASP-2 inhibitor comprising a sequence having at least 85%, 90%, 95%, 97%, 98%, 99%, or 100% homology with a sequence according to either SEQ ID NO: 1 or SEQ ID NO: 2; and 2) an additional cancer therapy agent. In an embodiment, the present disclosure provides methods for treating pancreatic cancer by administering to a subject in need thereof 1) an MASP-2 inhibitor comprising a sequence having at least 80% homology with a sequence according to either SEQ ID NO: 1 or SEQ ID NO: 2; and 2) another cancer therapy agent. In an embodiment, the present disclosure provides methods for treating pancreatic cancer by administering to a subject in need thereof 1) an MASP-2 inhibitor comprising a sequence having at least 85%, 90%, 95%, 97%, 98%, 99%, or 100% homology with a sequence according to either SEQ ID NO: 1 or SEQ ID NO: 2; and 2) another cancer therapy agent.

In an embodiment, the present disclosure provides methods for treating a cancer by administering to a subject in need thereof 1) an MASP-2 inhibitor comprising one or more sequences having at least 80% homology with a sequence according to SEQ ID NO: 1 and one or more sequences having at least 80% homology with a sequence according to SEQ ID NO: 2; and 2) an additional cancer therapy agent. In an embodiment, the present disclosure provides methods for treating a cancer by administering to a subject in need thereof 1) an MASP-2 inhibitor comprising one or more sequences having at least 85%, 90%, 95%, 97%, 98%, 99%, or 100% homology with a sequence according to SEQ ID NO: 1 and one or more sequences having at least 85%, 90%, 95%, 97%, 98%, 99%, or 100% homology with a sequence according to SEQ ID NO: 2; and 2) an additional cancer therapy agent. In an embodiment, the present disclosure provides methods for treating pancreatic cancer by administering to a subject in need thereof 1) a MASP-2 inhibitor comprising one or more sequences having at least 80% homology with a sequence according to SEQ ID NO: 1 and one or more sequences having at least 80% homology with a sequence according to SEQ ID NO: 2; and 2) an additional cancer therapy agent. In an embodiment, the present disclosure provides methods for treating pancreatic cancer by administering to a subject in need thereof 1) an MASP-2 inhibitor comprising one or more sequences having at least 85%, 90%, 95%, 97%, 98%, 99%, or 100% homology with a sequence according to SEQ ID NO: 1 and one or more sequences having at least 85%, 90%, 95%, 97%, 98%, 99%, or 100% homology with a sequence according to SEQ ID NO: 2; and 2) an additional cancer therapy agent.

Certain MASP-2 antibodies are disclosed in U.S. Pat. No. 11,008,404 B2, issued May 18, 2021 and which is incorporated by reference herein in its entirety. Certain MASP-2 antibodies are also disclosed in U.S. Pat. No. 10,189,909 B2, issued Jan. 29, 2019 and which is incorporated by reference herein in its entirety. Certain MASP-2 antibodies are also disclosed in International Patent Application Number PCT/

US2012/036509, filed May 4, 2012 and published as WO 2012/151481 on Nov. 8, 2012, which is incorporated by reference herein in its entirety. Such MASP-2 antibodies and antigen binding fragments thereof may be utilized in methods of treating cancer, more particularly in methods of administration for drugs, i.e. "Route of Administration". Examples of selected routes that are especially suitable for the present invention are shown below in Table 2. Additionally, a transnasal route may be utilized in various embodiments.

TABLE 2

Exemplary administration routes

| NAME | DEFINITION | SHORT NAME | FDA CODE | NCI* CONCEPT ID |
|---|---|---|---|---|
| INTRABRONCHIAL | Administration within a bronchus. | I-BRONCHI | 067 | C38225 |
| INTRAPERITONEAL | Administration within the peritoneal cavity. | I-PERITON | 004 | C38258 |
| INTRAPLEURAL | Administration within the pleura. | I-PLEURAL | 043 | C38259 |
| INTRAPULMONARY | Administration within the lungs or its bronchi. | I-PULMON | 414 | C38261 |
| INTRAVENOUS | Administration within or into a vein or veins. | IV | 002 | C38276 |
| LARYNGEAL | Administration directly upon the larynx. | LARYN | 364 | C38282 |
| NASAL | Administration to the nose; administered by way of the nose. | NASAL | 014 | C38284 |
| ORAL | Administration to or by way of the mouth. | ORAL | 001 | C38288 |
| OROPHARYNGEAL | Administration directly to the mouth and pharynx. | ORO | 410 | C38289 |
| RECTAL | Administration to the rectum. | RECTAL | 016 | C38295 |
| RESPIRATORY (INHALATION) | Administration within the respiratory tract by inhaling orally or nasally for local or systemic effect. | RESPIR | 136 | C38216 |
| TOPICAL | Administration to a particular spot on the outer surface of the body. | TOPIC | 011 | C38304 |
| TRANSDERMAL | Administration through the dermal layer of the skin to the systemic circulation by diffusion. | T-DERMAL | 358 | C38305 |
| TRANSMUCOSAL | Administration across the mucosa. | T-MUCOS | 122 | C38283 |

*National Cancer Institute treating pancreatic cancer. Additionally, antibodies and antigen-binding fragments comprising sequence(s) having at least 80% sequence homology with an antigen-binding portion of such MASP-2 antibodies may be utilized in methods of treating cancer, more particularly in methods of treating pancreatic cancer.

In various embodiments, a MASP-2 inhibitor may be administered along with, or may be present in a composition with, a further cancer therapy agent (such as a chemotherapeutic agent or other cancer treating medicine). In an embodiment, the administration is performed intravenously.

In an embodiment, the administration is performed by any known route of administration. The U.S. Food & Drug Administration has provided a standard for all routes of The term "pharmaceutically acceptable" is used herein with respect to the compositions, in other words the formulations, of the present invention, and also with respect to the pharmaceutically acceptable salts, esters, solvates, and prodrugs thereof. The pharmaceutical compositions of the present invention comprise a therapeutically effective amount of the active agents and a pharmaceutically acceptable carrier. These carriers can contain a wide range of excipients. Pharmaceutically acceptable carriers are those conventionally known carriers having acceptable safety profiles. The compositions are made using common formulation techniques. See, for example, *Remington's Pharmaceutical Sciences*, 17$^{th}$ edition, edited by Alfonso R. Gennaro, Mack Publishing Company, Easton, PA, 17th edition, 1985.

The term "subject" means a human patient or animal in need of treatment, therapy, or intervention for a cancer, such as pancreatic cancer.

The terms "treating" and its derivatives such as "treat" or "treatment," as used herein, may be used with respect to a particular condition, for example, a cancer or pancreatic cancer. In reference to a particular condition, "treating" and its derivatives are inclusive of several meanings, including (1) to alleviate one or more symptoms, effects, or side effects associated with the condition, (2) to ameliorate the condition and/or one or more of the biological manifestations or underlying causes of the condition, (3) to interfere with one or more of the biological manifestations or underlying causes of the condition or with one or more points in the biological cascade(s) associated with the condition, (4) to slow the progression of, or arrest the development of, the condition or of one or more of the biological manifestations of the condition, (5) to prevent or reduce the risk of a subject developing the condition, in some cases prophylactically when the subject has one or more risk factors for the condition or has been exposed to or infected with a virus being associated or having potential to cause the condition (6) to cause regression of the condition, or improvement or reversal of, the biological manifestations or underlying causes of the conditions. It can be appreciated that "treating" may encompass one or more of these meanings simultaneously and that a subject's condition may change over time or throughout the course of treatment such that the meaning of "treating" as applied to a given subject may change over time or throughout the course of treatment. "Treatment" could be in combination with other therapies or alone.

The term "first-line" in the context of "first-line cancer therapy" or, alternatively, "first-line cancer treatment" or "first-line treatment", generally refers to the first treatment given for treating a cancer. While the terms "treatment" and "therapy" can be used interchangeably, the term "therapy" can more particularly refer to a certain course of treatment as a part of an overall cancer treatment. The "first-line" therapy is often a field standard for a certain disease indication, or may be selected from one of multiple field standards or other treatment options based upon a physician's professional medical judgement. For example, in cancers which are denoted by different stages of progression, the "first-line" therapy may vary based upon the stage as well as other characteristics of the particular patient or disease presentation in the patient. A "first-line" cancer therapy may include a surgical procedure prior to, during, or after administration of a cancer therapy, and a "cancer therapy" as used herein generally contemplates surgical interventions where appropriate in addition to administration of a chemotherapeutic agent or other cancer drug. As should be evident, a surgical procedure is typically a discrete event whereas a cancer therapy is dosed continually over a treatment regimen. Additionally, a first-line cancer therapy may include radiation therapy as a discrete event or as an ongoing part of the first-line cancer therapy. As used herein, the term "first-line" is not intended to limit a given method of treatment in a manner requiring that the first-line treatment is actually a field standard; the physician may, in their professional medical judgement, use a non-standard or even experimental therapy as a "first-line" therapy. Therefore, the "first-line" therapy referenced herein is the first therapy given to the cancer patient in need thereof, generally after or concurrent with obtaining a biological sample from the patient for the purposes of evaluating a pre-treatment MASP-2 level.

A "second-line cancer therapy" as used herein refers to any subsequent cancer t therapy given after a "first-line" therapy has failed to reduce MASP-2 levels in the cancer patient. In such cases, a physician may discontinue the first line therapy and then commence administration of the second-line therapy. In some cases, there may be overlap in the discontinuing of the first line therapy and the commencement of the second-line therapy. In some cases, the second-line cancer therapy may still involve the first-line therapy (at a same or different treatment regimen) but the second-line therapy may include an additional cancer drug (such as an additional chemotherapeutic agent). A second-line cancer therapy may be a standard cancer therapy which could have been reasonably given as a first-line treatment but for the selection of a different first-line treatment. Alternatively, a second-line cancer therapy may be a non-standard or even experimental cancer therapy administered under the professional medical judgement of a physician. Likewise, third-line or further therapies are contemplated where both the first-line and second-line therapies fail to reduce MASP-2 levels.

When a biological sample is taken "prior to or at commencement" of the first-line cancer therapy, it is contemplated that the biological sample could still be taken at some time period after administration of the first-line cancer therapy, but before the first-line cancer therapy affects the baseline MASP-2 level of the patient. However, it is generally preferable to take the biological sample before the first-line cancer therapy is administered to ensure that the baseline MASP-2 level is uninfluenced by the cancer therapy. It is also contemplated that the baseline biological sample may include multiple biological samples at various pre-treatment time points.

When a first-line cancer therapy is discontinued, because MASP-2 levels in the patient did not decrease in response to the first-line cancer therapy, it does not generally mean that treatment of the patient will cease. In some cases, the same first-line cancer therapy may be continued, but at a different dosage or dosing regimen. In other cases, the same first-line cancer therapy may be continued in combination with a further therapy. For example, when the phrase "discontinuing administering the first-line cancer therapy according to the treatment regimen" or variants thereof are recited, it is intended to mean that either or both of the cancer therapy or the treatment regimen may be discontinued in favor of a different (second-line) cancer therapy, a different treatment regimen only using the same first-line therapy, or both. In that case, the discontinuing can include commencing administering the first-line cancer therapy according to a different treatment regimen, or discontinuing administration of any cancer therapy (for example to prevent unnecessary side effects where the cancer has progressed too far), or commencing administering a second-line cancer therapy instead of the first-line cancer therapy, at a treatment regimen of the second-line cancer therapy. After discontinuation of the first-line cancer therapy, the physician will generally rely upon their professional medical judgement to determine the subsequent treatment options. When a subsequent cancer therapy is given, the physician may continue to monitor MASP-2 levels to evaluate whether the subsequent cancer therapy elicits a better response.

A cancer therapy (including a first-line cancer therapy) is generally given according to a treatment regimen over a treatment time period. The treatment regimen can generally be pre-determined, meaning that the physician has decided upon a certain treatment regimen by which the cancer therapy will be administered to the patient. The "treatment regimen" generally includes the dosage (i.e., amount of drug) of each administration, as well as the dosing regimen by which the dosages are administered (such as three-times daily, twice-daily, daily, every other day, every second day, every third day, every fourth day, every fifth day, every sixth day, weekly, bi-weekly, and so on). The treatment regimen may include other details such as the time of day for the administration(s), whether before or after a meal, etc.

As indicated, the first-line treatment is generally given over a "treatment time period". This treatment time is generally the period of time over which the first-line treatment is given before an intervening event occurs, such as a decision by the medical professional to discontinue the first-line treatment or modify the treatment regimen (because MASP-2 levels have not decreased relative to the baseline), cancer remission, or severe disease progression/death. MASP-2 levels determined during the course of treatment are generally referred to as "treatment MASP-2 levels" or grammatical variations thereof which differ from "baseline MASP-2 levels" or grammatical variations thereof which are taken prior to or at commencement of the first-line cancer therapy. An overall cancer treatment for a given patient may include multiple treatment time periods, each treatment time period corresponding to a particular therapy being given according to a treatment regimen in conjunction with MASP-2 level monitoring to direct the overall treatment.

In various embodiments herein, one or more treatment MASP-2 levels are determined at one or more timepoints over the course of the treatment time period. For simplicity, an exemplary method may comprise determining a treatment MASP-2 level and it is explicitly contemplated that multiple treatment MASP-2 levels may be determined in such methods at various timepoints. The timepoints may be selected, scheduled, recurring, or variable so long as treatment MASP-2 levels after commencing a cancer therapy can be evaluated. To evaluate efficacy of the cancer therapy at the treatment regimen, the physician compares the one or more treatment MASP-2 levels to the baseline MASP-2 level. Particular patients may have different disease progression(s) and the physician may use their professional medical judgement to determine whether or not the treatment MASP-2 levels for the patient are generally decreasing. The terms "generally decreasing" or "have generally decreased" do not mean that each and every treatment MASP-2 level has decreased relative to the baseline, taking into account the possibilities of variability and of error in any empirical measurement; however, it usually means that a majority of treatment MASP-2 levels have decreased and/or there is an observable trend of decreasing MASP-2 levels as a function of time. In some cases, particularly where few treatment MASP-2 levels are collected, it may be the case that a majority of MASP-2 levels have not decreased but the physician may, by their professional medical judgement, infer that MASP-2 levels are generally decreasing or have generally decreased in view of the timing after commencement of therapy at which the biological samples were collected and respective treatment MASP-2 levels were determined. This is because some amount of time is needed after commencement of therapy to observe changes in MASP-2 levels. The amount of time needed to observe changes in MASP-2 levels may vary by the particular cancer indication (type, stage, other indications of the patient, etc.) or cancer therapy and may be about a week, about two weeks, about three weeks, about four weeks, about a month, about 1.5 months, about 2 months, about 2.5 months, about 3 months, about 4 months, etc. In some embodiments, the amount of time at which a discernible MASP-2 level difference is observable ranges from about 2 weeks to about 4 months. In some embodiments, the amount of time at which a discernible MASP-2 level difference is observable is about 1 month, or about 2 months, or about 3 months. In some embodiments, the amount of time at which a discernible MASP-2 level difference is observable is about 2 months. In these contexts, the term "about" means±5 days with respect to a quantity given in week(s), or ±15 days with respect to a quantity given in month(s). Based on the time needed to observe changes in MASP-2 levels, the healthcare provider can determine appropriate time points at which to obtain samples from the patient for an MASP-2 level determination.

In some embodiments, for example if a baseline MASP-2 level was not determined due to not collecting a biological sample prior to commencement of a cancer therapy, or due to some other error or circumstance, the requirement of obtaining a biological sample from the patient prior to or at commencement of a first-line cancer therapy can be met by a treatment MASP-2 level obtained shortly after beginning the cancer therapy. In such cases, the physician will not be able to compare the other, later treatment MASP-2 levels to a true baseline but may still observe a trend that the MASP-2 levels are generally decreasing, evidencing treatment efficacy. That is, and as previously stated, in some embodiments, "prior to or at commencement" may include a treatment MASP-2 level which is close enough in time to the commencement of therapy that it can be equivalently or essentially treated as a baseline MASP-2 level to effectuate treatment decisions by a medical professional.

In an embodiment, a threshold MASP-2 percentage decrease is utilized by the physician (alone or in combination with standard-of-care assessments) to determine whether or not a patient is responding to the cancer therapy. For example, in some embodiments, if the treatment MASP-2 level has a percent decrease from the baseline MASP-2 level greater than or equal to a threshold percent decrease, then the first-line cancer treatment may be continued. The percentage decrease may be calculated as shown by Eqn. 1 below:

$$\% \text{ Decrease} = \left(\frac{\text{(Baseline } MASP2 \text{ Level} - \text{Treatment } MASP2 \text{ Level})}{\text{Baseline } MASP2 \text{ Level}}\right) \times 100 \qquad \text{EQN. 1}$$

The observable quantity of percent decrease may then be compared to a threshold percent decrease to determine whether the observed reduction in MASP-2 during treatment is sufficiently high to indicate that the first-line treatment is effective. For example, if a target threshold percent decrease is established at 10% and a 12% decrease in MASP-2 levels is actually observed as a result of the first-line treatment, then the first-line treatment may be continued because the target threshold percent decrease was exceeded. Alternatively, if a 4% decrease in MASP-2 levels is observed as a result of the first-line treatment, the physician may either change the dosing regimen (increase dosage, dosage frequency, etc. of the first-line treatment), or may substitute the first-line treatment for a different second-line treatment, because the target threshold percent decrease of 10% was not met or exceeded.

In various embodiments, the threshold percent decrease is a decrease of at least about 10%, or at least about 20%, or at least about 30%, or at least about 40%, or at least about 50%, or at least about 60%, or at least about 70%, or at least about 80%. In a particular embodiment, the threshold percent decrease is a decrease of at least about 10%. In the context of percent decrease and threshold percent decrease values, the term "about" is intended to encompass percentages having a value within ±5% of the given value. In another particular embodiment, the threshold decrease is a decrease of 10%.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Figure 2:
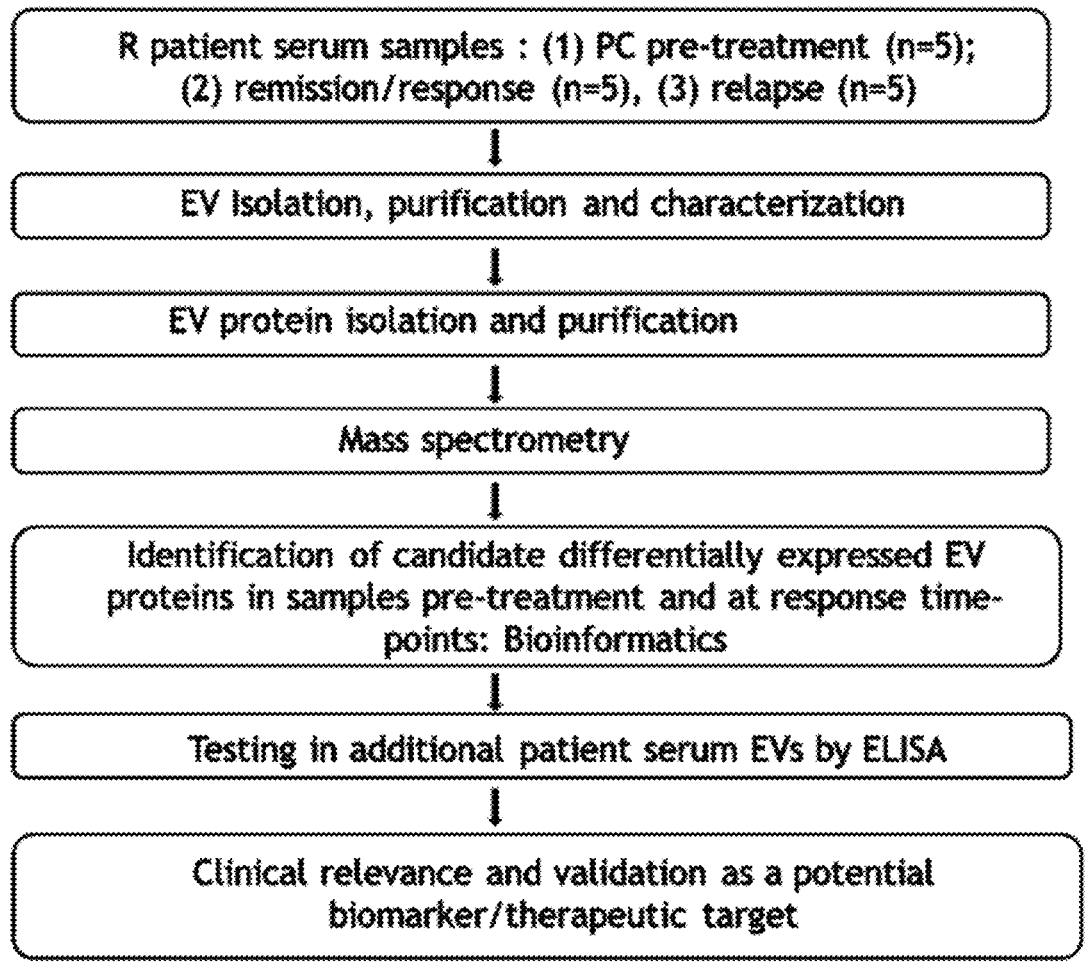
FIG. 2—Schematic of an exemplary experimental workflow.

MASP-2 was first identified as an important biomarker from patient studies performed in connection with this disclosure. These studies were utilized to identify the differences in serum and serum extracellular vesicle (EV) proteins in advanced pancreatic cancer patients at diagnosis (pre-treatment), remission (during treatment), and relapse (during treatment) to discover novel candidates that may serve as (1) a marker for chemotherapeutic responsiveness or cancer remission, and (2) a target for advanced cancer therapy. See, for example, FIG. 1 depicting an exemplary diagram of an extracellular vesicle (EV), and FIG. 2 depicting an exemplary biomarker discovery method.

Pancreatic cancer patient serum specimens were utilized to identify measurable blood biomarkers of pancreatic cancer that have heretofore not been linked to the disease. Presently, the only clinically utilized blood biomarker for monitoring treatment response in pancreatic cancer is to detect changes in the serum marker CA19-9. Although a >75% reduction in CA19-9 does typically correlate with response to treatment, CA19-9 may increase in some responding patients and decrease (less than 75% of baseline levels) in non-responding patients, making it less than an ideal marker. That is, a physician cannot reliably predict, or measure treatment efficacy based on CA19-9 levels alone. Moreover, certain medical conditions (hyperbilirubinemia from obstructive jaundice) alter CA 19-9 levels, making it an unusable biomarker in patients having such medical conditions.

The current invention addresses this challenge based upon the discovery that levels of MASP-2, more particularly EV-MASP-2, is a novel biomarker to guide clinicians in assessing the response of their cancer patients (such as pancreatic cancer patients) to chemotherapy and other drug treatments. The findings herein further suggest that MASP-2 may itself potentially serve as a therapeutic target for cancer treatment, more particularly for pancreatic cancer treatment.

Example 1: Classification of Patient Groups Based on Response to Chemotherapy Enrolled pancreatic cancer (PC) patients at stages III and IV who received either FOLFIRINOX or gemcitabine/abraxane chemotherapy regimens as first-line treatment were classified into two distinct groups: Responders (R) and Non-Responders (NR). The R group consisted of patients who responded to chemotherapy, as indicated by >75% decline in the tumor marker CA 19-9 for a minimum of two consecutive months and survival of at least six months; responses were confirmed by CT scans that showed either stable or improving primary and metastatic lesions. On the other hand, the NR patient group was defined as receiving at least one dose of chemotherapy and having died due to PC progression within six months. Only patients with a follow-up serum sample at least one month after starting treatment were included in the NR group. Table 1 below outlines the demographics of the patients involved in this study, while FIG. 4 illustrates a consort diagram detailing the composition of the study cohort.

TABLE 1

Demographic and clinical characteristics of the advanced pancreatic cancer patient cohorts.

| | R (n = 27) | NR (n = 11) | p-value* |
|---|---|---|---|
| Age, median (range) | 68 (44-89) | 76 (49-86) | 0.411 |
| Sex, n (%) | | | |
| Female | 18 (67) | 04 (36) | 0.147 |
| Male | 09 (33) | 07 (64) | |
| Race, n (%) | | | |
| Caucasian | 24 (89) | 10 (91) | 1.000 |
| Other | 03 (11) | 01 (09) | |
| BMI, median (range) | | | |
| median (range) | 25 (19-38) | 25 (19-32) | 0.690 |
| Diabetes, n (%) | 06 (22) | 04 (36) | 0.432 |
| Stage, n (%) | | | |
| III | 06 (22) | — | 0.153 |
| IV | 21 (78) | 11 (100) | |
| Liver Metastasis, n (%) | 17 (63) | 09 (82) | 0.443 |
| Performance status ECOG >1, n(%) | 01 (04) | 01 (09) | 0.500 |
| CA 19-9 U/mL | | | |
| median (range) | 840 (01-132750) | 3511 (01-476300) | 0.824 |
| Negative (<37), n (%) | 02 (08) | 03 (27) | 0.134 |
| Elevated (>100), n (%) | 24 (89) | 07 (64) | 0.161 |
| Elevated (>1000), n (%) | 13 (48) | 07 (64) | 0.485 |
| First line chemotherapy, n (%) | | | |
| FOLFIRINOX | 13 (48) | 02 (18) | 0.145 |
| Gemcitabine/Nab-paclitaxel | 14 (52) | 09 (82) | |

*Fisher's exact test tow-tailed p-value for categorical and Wilcoxon p-value for continues variable was used.

Example 2: Patient Serum Exosome Isolation and Characterization

Extracellular vesicles from serum aliquots were isolated using Izon qEV Isolation columns (Izon Science LTD), which rely on size-exclusion chromatography following the manufacturer's protocol. Fractions 1-3 containing the most purified EVs were combined and utilized for downstream in vitro assays.

Figure 4A:
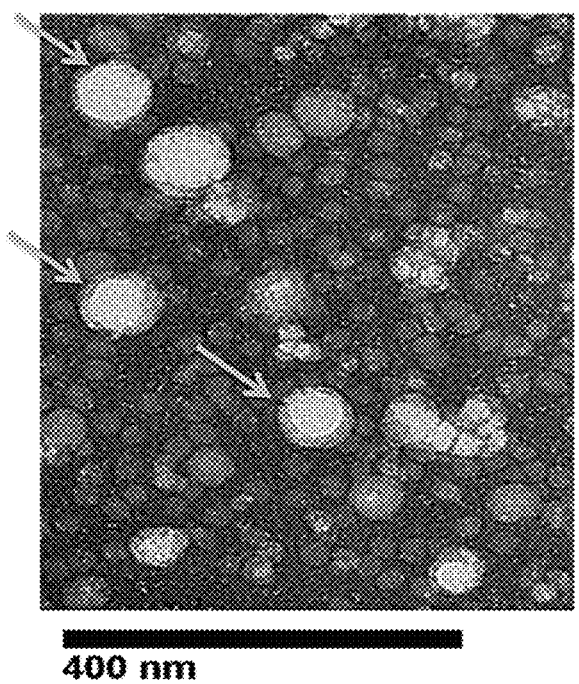
FIGS. 4A and 4B—(4A) Exemplary SEM image of EVs isolated from plasma and (4B) Exemplary size distribution of EVs isolated from plasma.
Figure 4B:
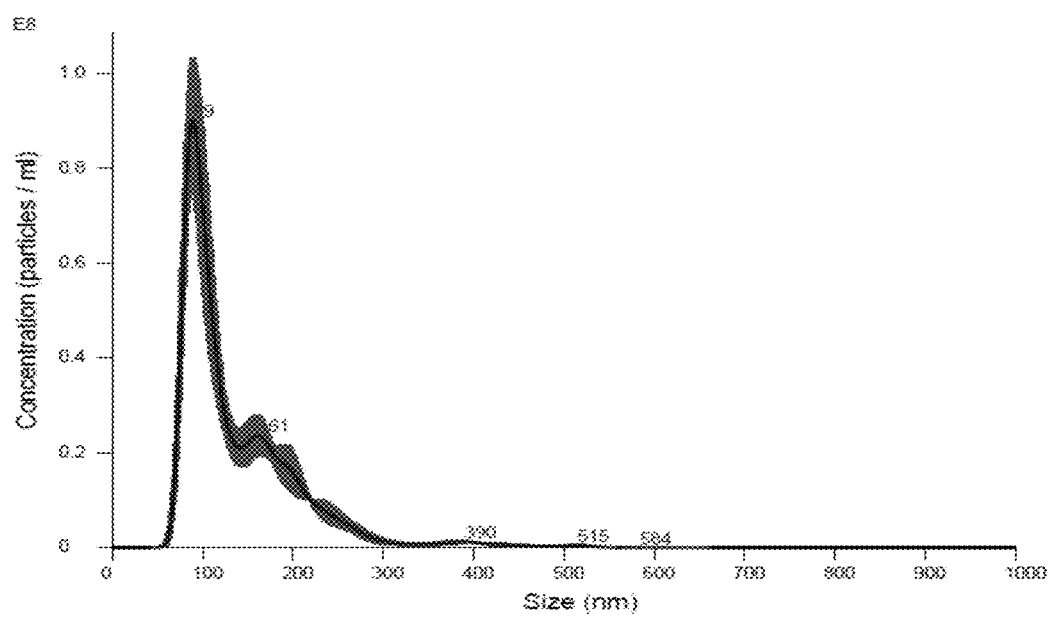

FIG. 4A depicts a representative image of EV morphology assessed by transmission electron microscopy (TEM). FIG. 4B depicts a representative concentration and particle size distribution. The concentration and size distribution of these collected EVs were assayed by a dynamic light-scattering technology-Nanoparticle Tracking Analysis (NTA) using a Nanosight NS300 instrument (Malvern Panalytical). The identity of the isolated fractions were confirmed by measuring the exosomal cell-surface markers such as CD9, CD63, and CD81, and tsg101 by Western blots. In addition to the size-exclusion chromatography-based EV isolation, EVs were isolated by chemical-affinity based technology utilizing EVtrap beads (PMID 32396726) by Tymora Analytical for mass spectrometry analysis for detection of the candidate proteins. Proteins obtained from EVs isolated by both the methods were validated, and results confirmed showing similar outcomes in the tested protein levels/distribution in the samples.

Example 3: Protein Isolation and Mass-Spectrometry

Figure 5A:
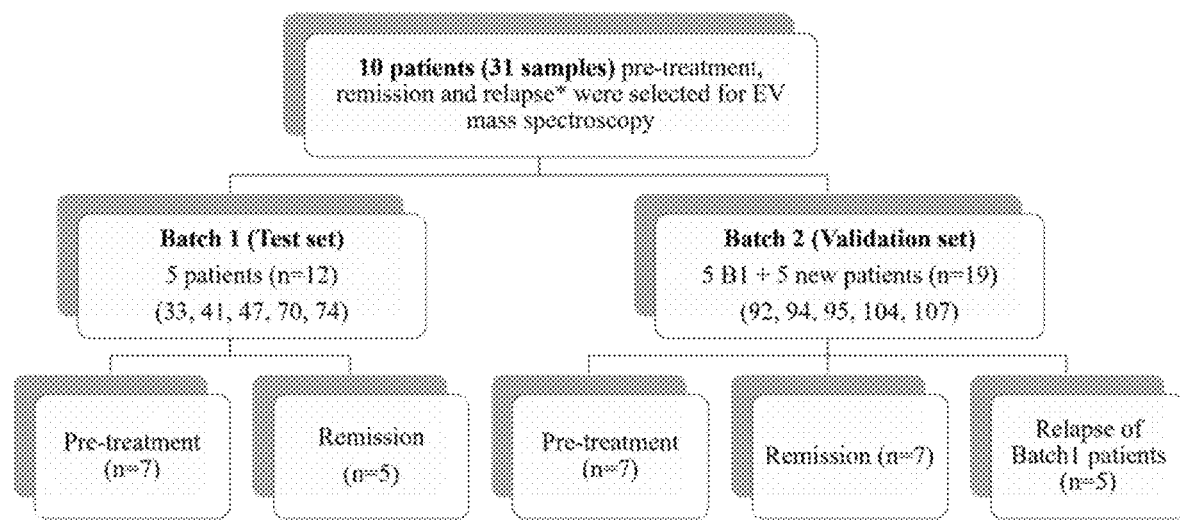
FIGS. 5A-5F—Workflow for identification of differentially expressed EV protein cargo by mass spectrometry. (5A) Schematic for experimental setup and replication sets for mass spectrometry. (5B) Venn diagram depicting overlapping and unique DE EV proteins between pre-treatment, remission and relapse timepoints from mass spectrometry data. Volcano plot illustrating the log fold-change and corresponding p values for DE proteins between (5C) pre-treatment and remission, (5D) remission and relapse, and (5E) pre-treatment and relapse. Significantly sections with upregulated and downregulated proteins (|fold change|≥1.4, x-axis; post-hoc Tukey HSDp value ≤0.05, y-axis) are labelled. (5F) Two-way hierarchical clustering performed by the Ward method for the nine candidate proteins based on their abundance in the five patients. Grayscale gradient indicates protein abundance, with darker shades representing higher abundance. Dotted areas denote lower abundance regions.

Serum samples from five patients, spanning the three timepoints, were processed for EV isolation and protein extraction, and mass spectrometry services were paid for through a commercial vendor. To ensure reproducibility and assess batch effects, samples were analyzed in replicates and divided into two batches (FIG. 5A). The first batch (test set) included 12 samples: five each from pre-treatment and remission, with two duplicated pre-treatment samples (n=7) for replication accuracy testing. The second batch (validation set) comprised 19 samples, including duplicates of pre-treatment and remission samples from two patients in batch 1, along with samples from the two timepoints in five additional patients. Additionally, relapse samples from the initial five patients from batch 1 were also included. Pearson correlation analysis indicated strong correlations between replicates within and across batches. RAW files obtained from mass spectroscopy were aligned against Homo Sapiens Uniprot database with no redundant entries using SEQUEST search engine and protein abundance was normalized with the total peptide amount. These protein abundance files obtained from the vendor were then used for bioinformatics analysis for the identification of the differentially expressed protein markers.

Figure 5B:
Figure 5C:
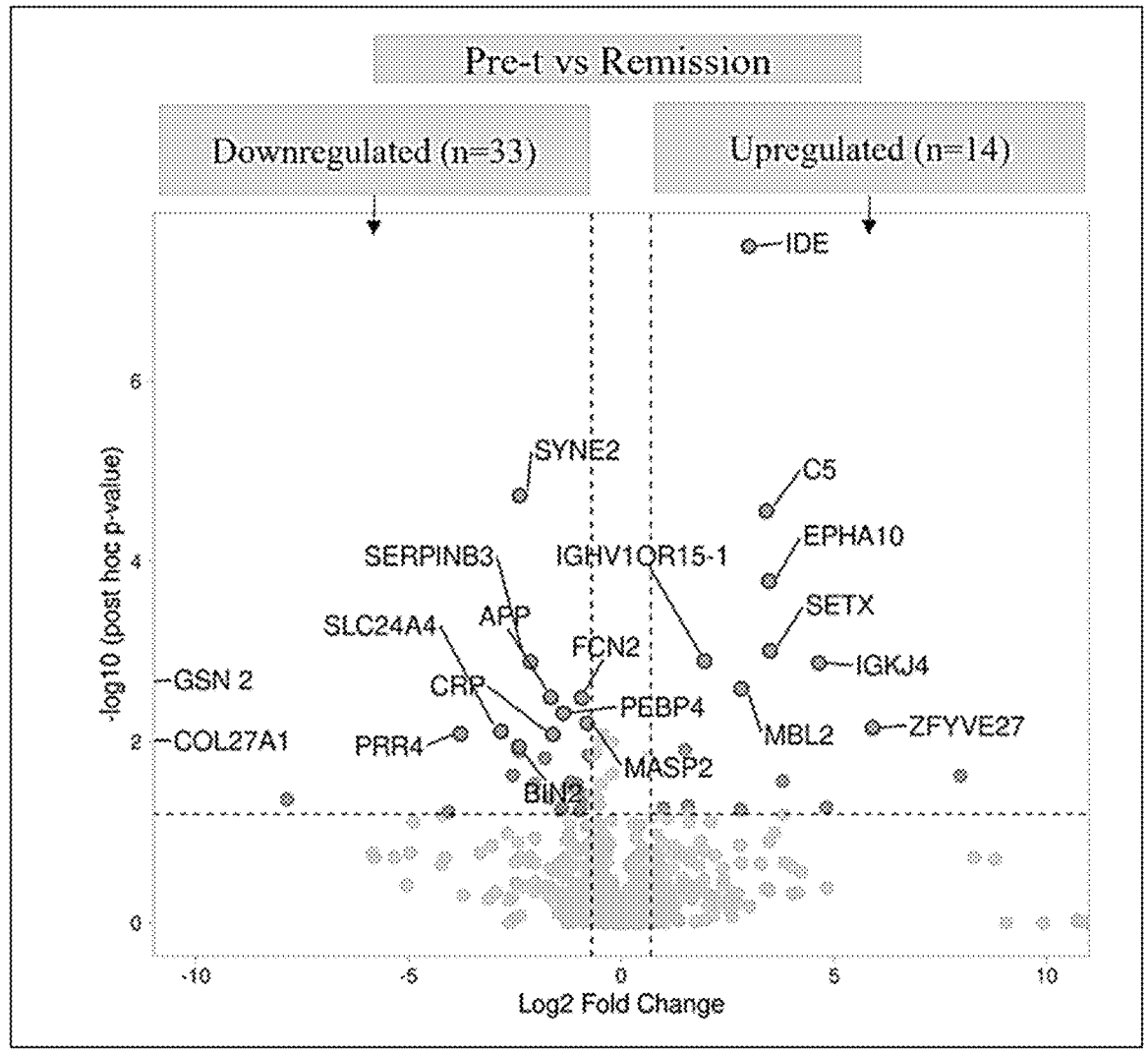
Figure 5D:
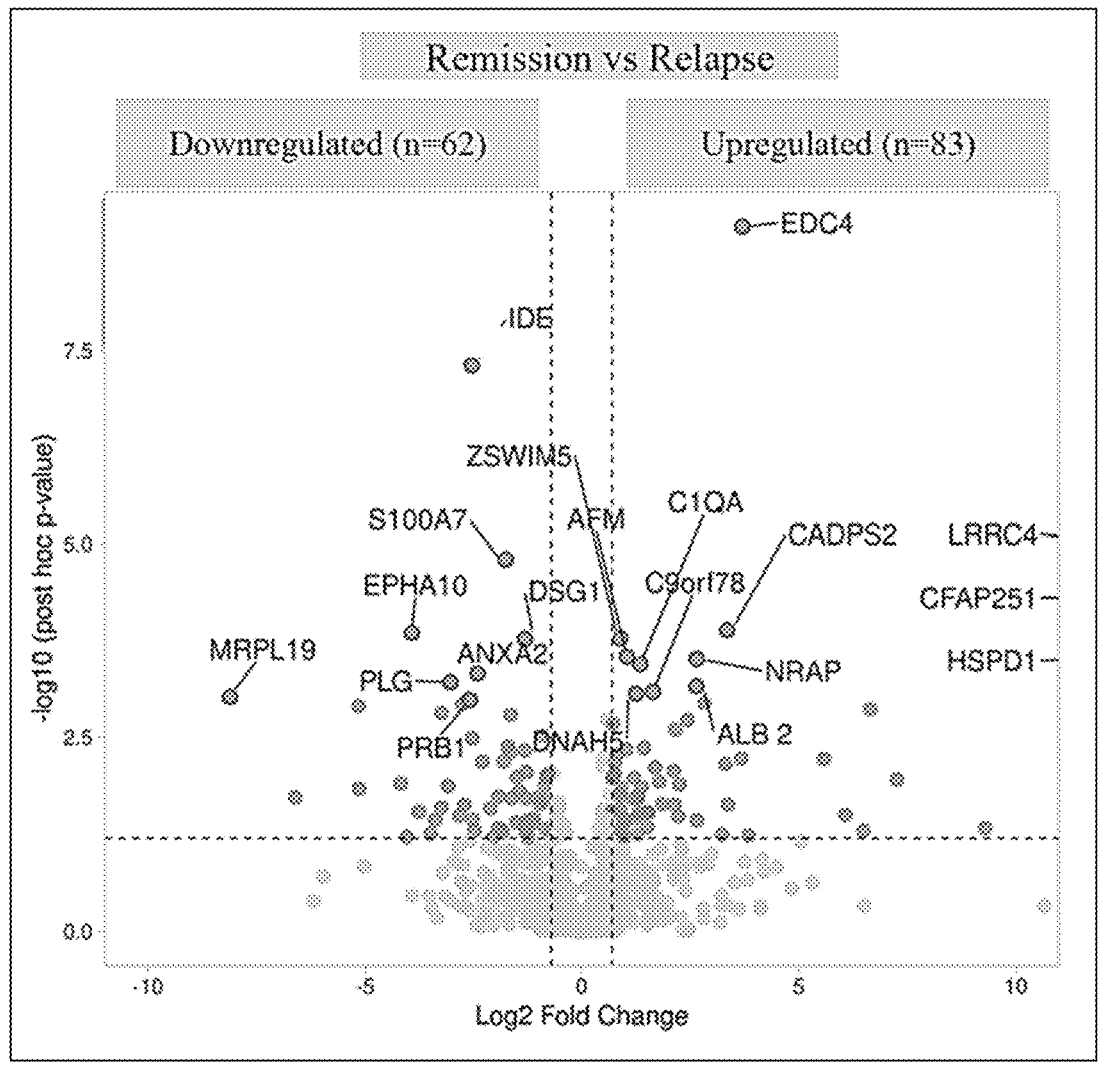
Figure 5E:
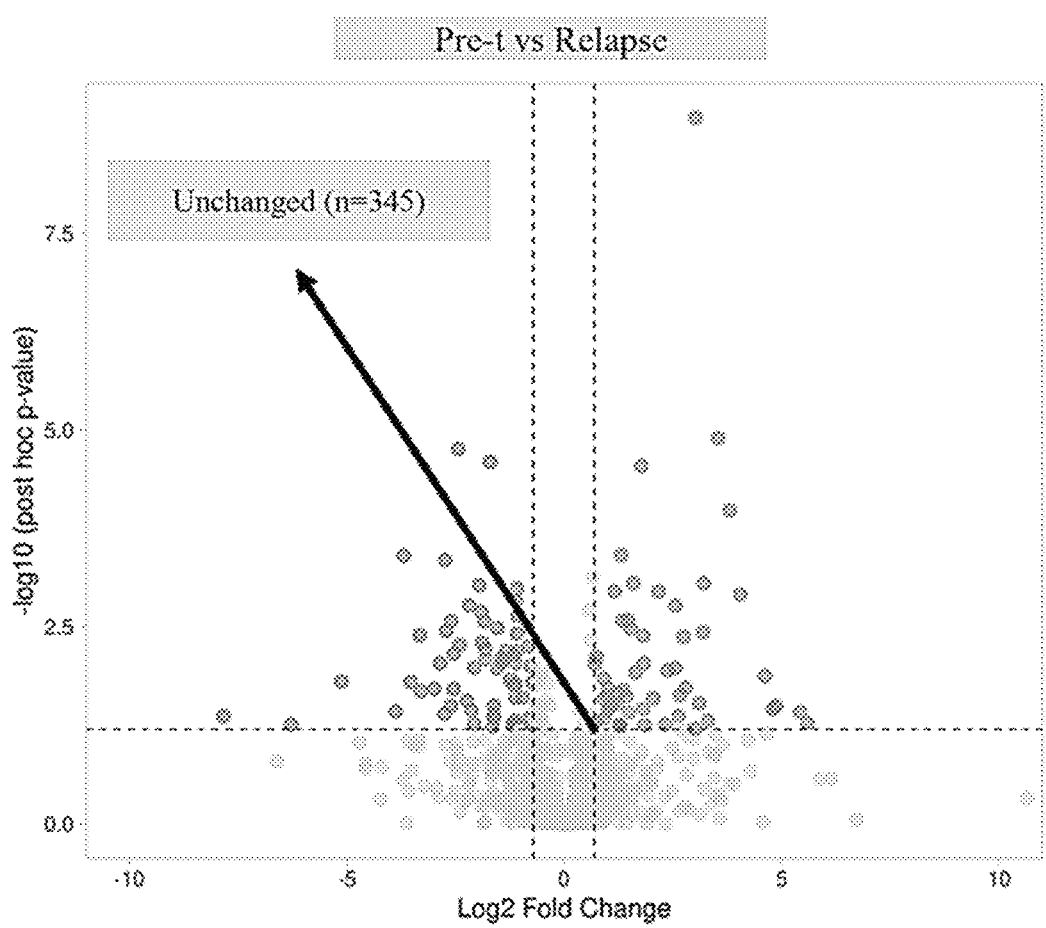

Bioinformatic analysis: The protein identification method involved a comprehensive analysis of proteomic data obtained from samples collected at three distinct stages: pre-treatment, remission, and relapse. Differential Expression (DE) analysis was performed for comparisons between pre-treatment vs remission, remission vs relapse, and pre-treatment vs relapse groups. To ensure robustness and minimize errors, a stringent post hoc analysis using the Tukey HSD test was applied, with a significance threshold of $p<0.05$. With the two criteria—a fold change of 1.4 and $p<0.05$—a total of 47 proteins exhibited significant DE between the pre-treatment and remission stages (FIGS. 5B&5C). Concurrently, 145 proteins displayed discernible segregation between the remission and relapse conditions (FIGS. 5B&5D). The analysis revealed 345 proteins exhibiting similar expressions when comparing serum EVs from the pre-treatment and relapse phases (FIGS. 5B&5E).

Figure 5F:
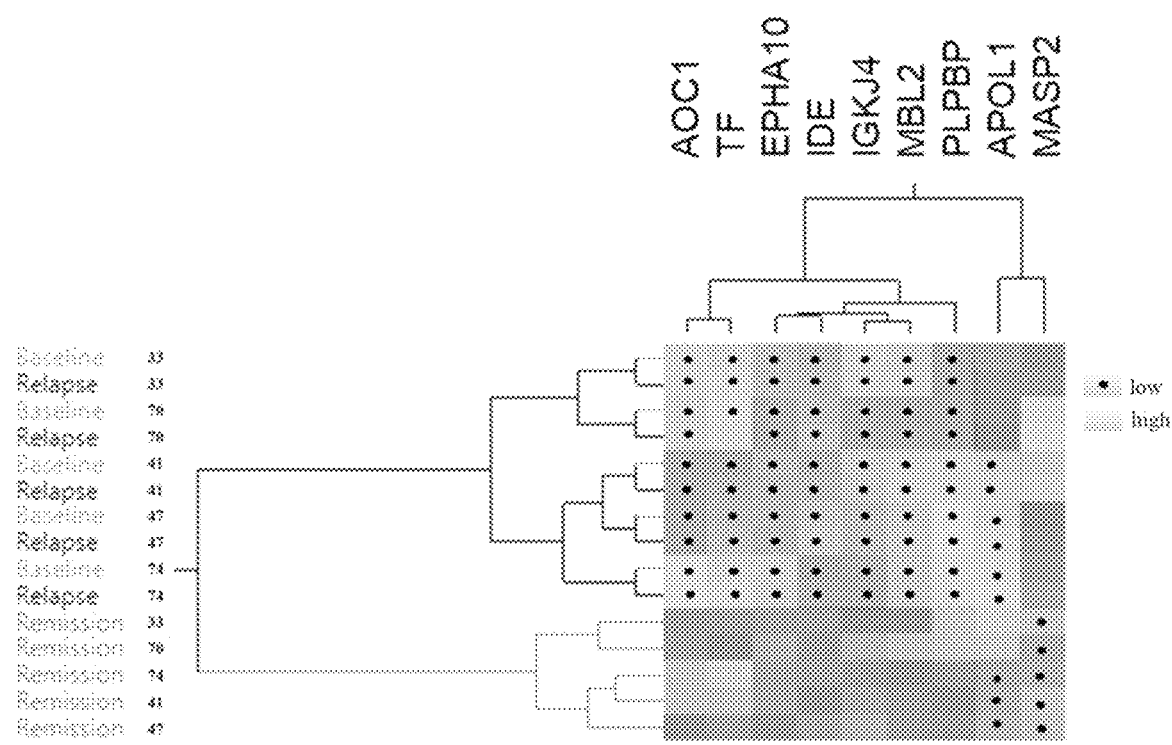

To identify proteins associated with pancreatic cancer remission, we prioritized those showing significant changes in one direction when comparing pre-treatment and remission timepoints, while moving in the opposite direction when comparing remission and relapse timepoints. Moreover, we ensured that the protein levels remained statistically non-significant between pre-treatment and relapse, emphasizing their relevance specifically during the remission phase of PC. This criterion identified a total of nine proteins, out of which seven proteins namely Insulin Degrading Enzyme (IDE), EPH Receptor A10 (EPHA10), Immunoglobulin Kappa Joining 4 (IGKJ4), Mannan-Binding Lectin 2 (MBL2), Transferrin (TF), Pyridoxal Phosphate Binding Protein (PLPBP), and Amine Oxidase Copper Containing 1 (AOC1) exhibited upregulation during remission compared to pre-treatment but downregulation during relapse compared to remission. On the other hand, two proteins, Mannan-Binding Lectin Associated Serine Protease 2 (MASP-2) and Apolipoprotein L1 (APOL1), showed downregulation during remission compared to pre-treatment but were upregulated during the relapse phase relative to remission (Table 2, below). In addition, unsupervised hierarchical clustering analysis of the nine identified proteins showed a distinct separation between samples collected at pre-treatment and remission, as well as between remission and relapse timepoints (FIG. 5F).

TABLE 2

Fold changes and significance of the top nine identified serum EV protein candidates.

| Protein Name | Pre-t vs Remission | | | | Remission vs Relapse | | | |
| --- | --- | --- | --- | --- | --- | --- | --- | --- |
| | Min | Max | p-Value | $\log_2$FC | Min | Max | p-Value | $\log_2$FC |
| IDE | 8.99E+06 | 2.72E+08 | 3.24E−08 | 3 | 3.49E+07 | 2.72E+08 | 4.95E−08 | −2.55 |
| EPHA10 | 2.54E+03 | 5.32E+06 | 0.00017 | 3.47 | 0.00E+00 | 5.32E+06 | 0.00014 | −3.93 |
| IGKJ4 | 0.00E+00 | 7.92E+06 | 0.00134 | 4.65 | 0.00E+00 | 7.92E+06 | 0.00124 | −5.15 |
| MBL2 | 3.13E+05 | 1.17E+08 | 0.00259 | 2.82 | 2.20E+06 | 1.17E+08 | 0.00323 | −2.54 |
| MASP2 | 2.33E+07 | 6.84E+07 | 0.00622 | −0.8 | 2.33E+07 | 6.28E+07 | 0.00913 | 0.76 |
| APOL1 | 9.63E+08 | 2.82E+09 | 0.04685 | −0.74 | 9.63E+08 | 2.86E+09 | 0.01844 | 0.86 |
| TF | 2.93E+08 | 9.22E+08 | 0.01469 | 0.65 | 4.52E+08 | 9.22E+08 | 0.02888 | −0.55 |
| PLPBP | 0.00E+00 | 5.10E+05 | 0.04291 | 18.28 | 0.00E+00 | 5.10E+05 | 0.04291 | −18.28 |
| AOC1 | 0.00E+00 | 6.13E+05 | 0.0442 | 18.52 | 0.00E+00 | 6.13E+05 | 0.04419 | −18.52 |

Figure 6:
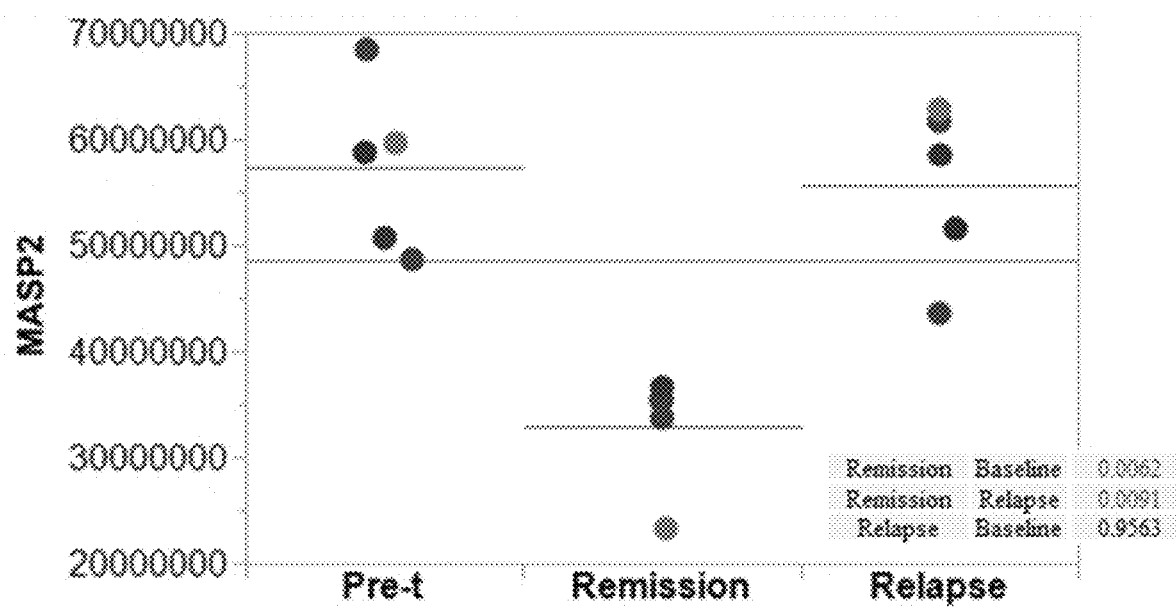
FIG. 6—Differential expression of MASP-2 protein levels in five patients from the responder (R) group at pre-treatment (baseline), remission, and relapse timepoints obtained by mass spectrometry.
Figure 7:
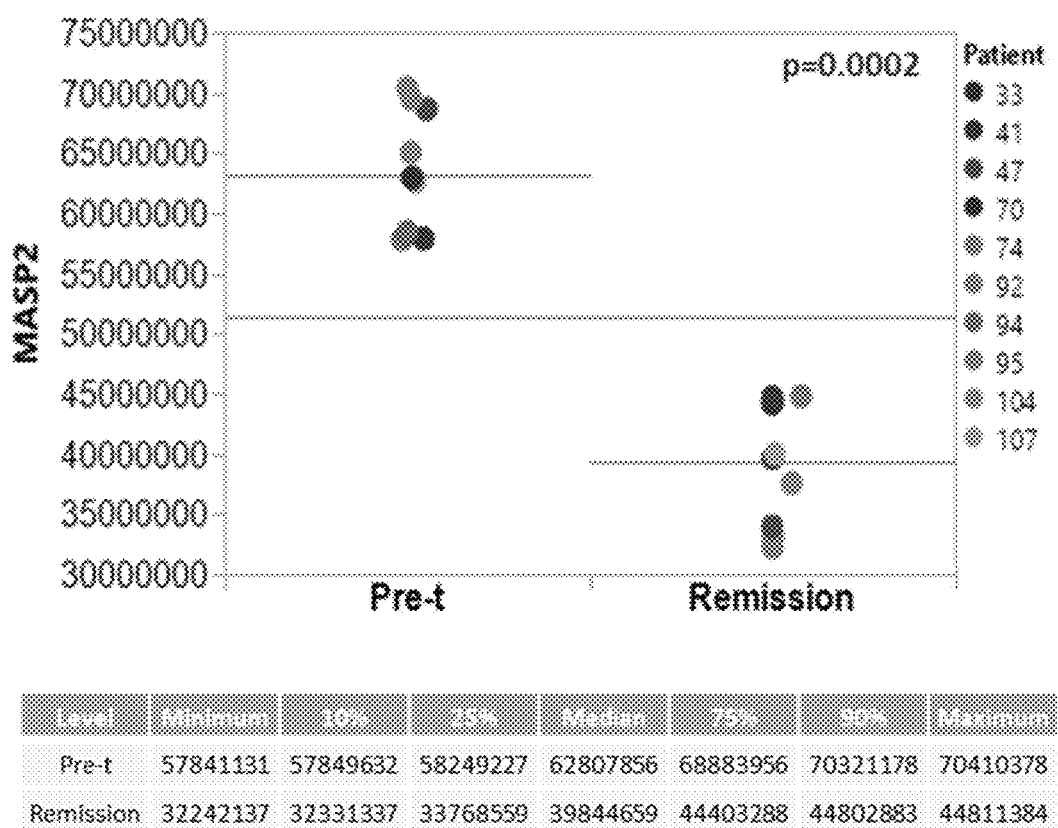
FIG. 7—MASP-2 protein levels by mass spectrometry in patients at pre-treatment (baseline) and remission combining two independent trials (n=10).

EV-MASP-2 levels exhibited the greatest segregation comparing remission to baseline in the 10 patients tested combining Batches 1 and 2. After further investigation into the mass spectrometry data, we identified protein MASP-2 exhibiting the most clear distinction in remission compared to pre-treatment baseline and relapse timepoints in the patient serum EVs (FIG. 6). Further, the trends were consistent in pancreatic cancer patients at the given timepoints in our two independent mass spectrometry runs (FIG. 7). Together, this data demonstrates that changes in EV-MASP-2 is an important predictor of response to first-line chemotherapy or remission in pancreatic cancer patients.

MASP-2 is a protein that is a component of the human immune system, part of the mannan-binding lectin (MBL) pathway of the complement system. MASP-2 levels are presently not measured as a standard of care in human normal or diseased conditions. There are only rare scientific reports of detecting MASP-2 as a component of circulating extracellular vesicles. Furthermore, there are no reports of MASP-2 in pancreatic cancer. Finally, there have been no reports in the scientific/medical literature linking MASP-2 to pancreatic cancer growth or response to chemotherapy.

Example 4: Larger Cohort Studies

With the discovery of EV-MASP-2 as a potential marker for cancer remission (more particularly for pancreatic cancer remission) we next sought to demonstrate if our findings remain consistent in a larger cohort of patients with advanced pancreatic cancer. To this end, we utilized longitudinally collected serum samples from (A) Responders (R) at (i) pre-treatment, (ii) remission, and (iii) relapse; and (B) Non-Responders (NR) at (i) pre-treatment and (ii) post-treatment, where no response to chemotherapy was observed. Serum EVs were lysed, and 10 μg of the extracted protein from each sample was subjected to ELISA using a MASP-2 ELISA kit (Cat #ab278121, Abcam). The ELISA assay on EVs in a larger cohort of R patient group (n=27) indicated that 63% patients showed at least a 20% drop in EV-MASP-2 levels during remission. Interestingly, 64% of these patients who experienced a relapse (n=22) showed at least 20% rise by a rise in EV-MASP-2 at relapse compared to remission timepoint.

Figure 8A:
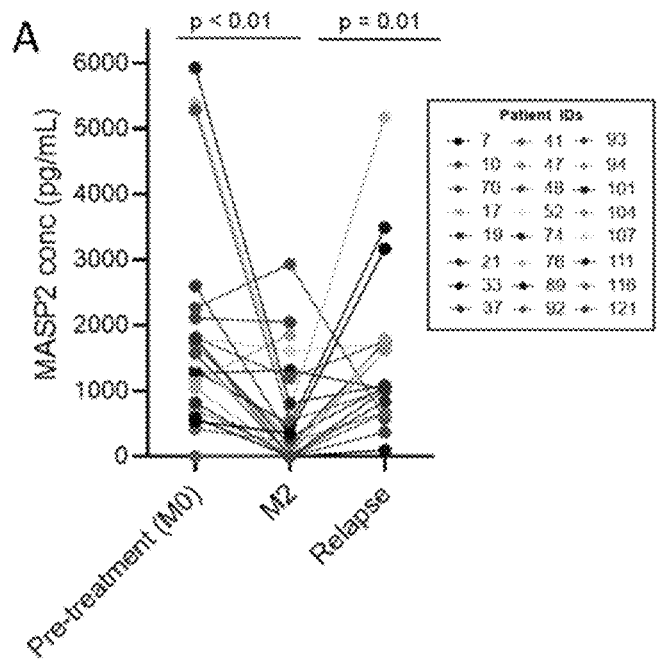
FIGS. 8A and 8B—MASP-2 protein concentrations (pg/mL) measured by ELISA in serum EV protein in patients belonging to the R group (n=24). (8A) Changes in MASP-2 concentration in individual patients at pre-treatment, month 2 (M2), and relapsetimepoints. Color-coded legends indicate patient IDs. (8B) Mean MASP-2 concentrations at the two tested timepoints.
Figure 8B:
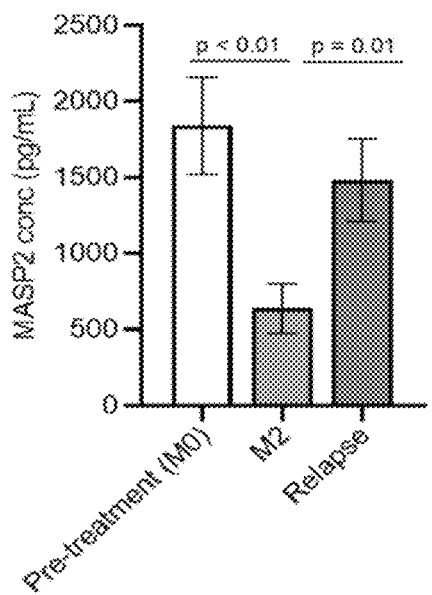

Our "remission" timepoint paralleled the nadir value in CA 19-9, which has been shown to occur after four months of treatment. While this nadir value does portend prolonged survival, it is not useful as an early predictor of chemotherapy effectiveness. A biomarker with such predictive capability would be valuable in avoiding futile therapy before the onset of toxic effects or tumor progression. Therefore, we investigated whether changes in EV-MASP-2 after 2 months (M2) of chemotherapy could serve as a predictor of chemotherapy responsiveness or non-responsiveness. As shown in FIGS. 8A&8B, ELISA assays indicated that compared to baseline, at month 2, EV-MASP-2 values were reduced to an even greater degree than at the remission timepoint. Interestingly, M2 EV-MASP-2 levels were reduced in several patients who did not exhibit a significant drop in EV-MASP-2 levels at the remission timepoint (Patient IDs 017, 021, 033, 037, 070, and 104). In total, 75% of the R group patients (n=24) demonstrated >20% reduction in EV-MASP-2 levels at month 2 compared to their pre-treatment levels. In addition, 85% of the patients who experienced a cancer relapse (n=20) exhibited at least a 20% increase in EV-MASP-2 levels from month 2 to the point of relapse. A groupwise comparison between pre-treatment vs. month 2 and relapse vs. month 2 depicted an overall significance in the changes in EV-MASP-2 levels among the tested timepoints (p=0.0001 and p=0.01 respectively; FIGS. 8A&B).

Figure 9A:
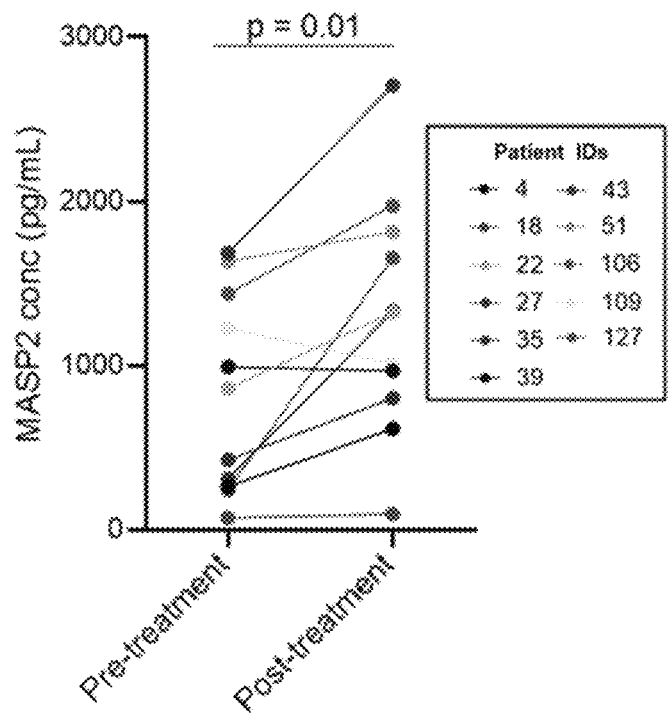
FIGS. 9A and 9B—MASP-2 protein concentrations (pg/mL) measured by ELISA in serum EV protein in patients belonging to the NR group (n=11). (9A) Changes in MASP-2 concentration in individual patients at pre- and post-chemotherapeutic treatment. Color-coded legends indicate patient IDs. (9B) Mean MASP-2 concentrations pre- and post-treatment in NR patients.
Figure 9B:
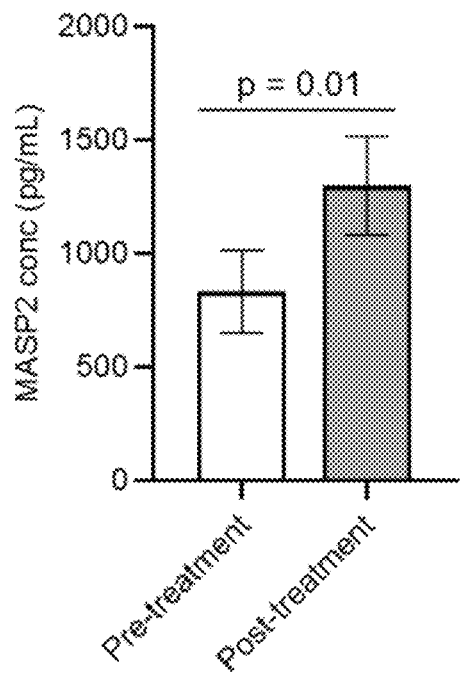
Figure 10:
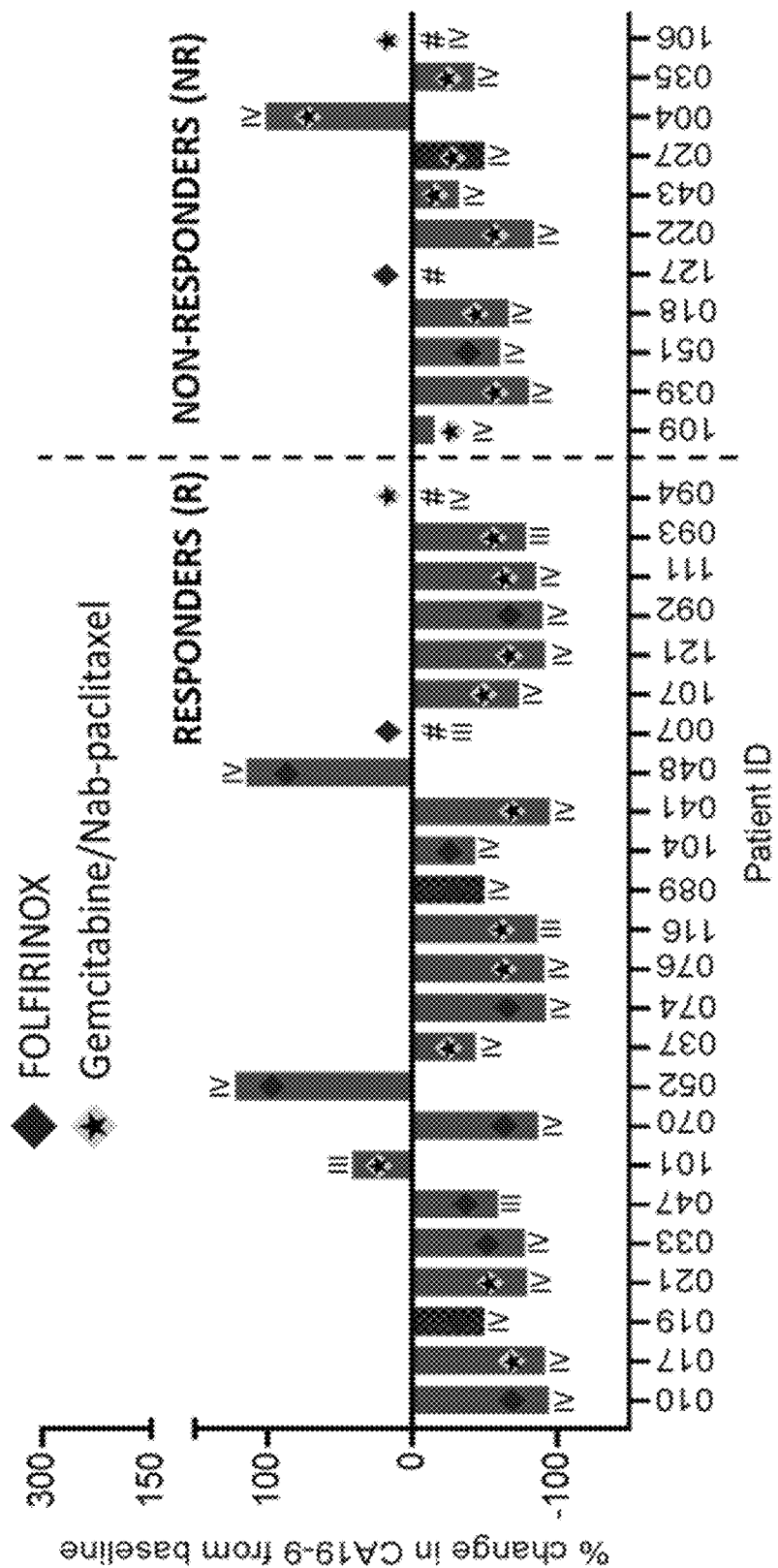
FIG. 10—Waterfall plot depicting percentage changes in CA 19-9 levels in serum EVs of R and NR patient groups 2 months post treatment compared to baseline (pre-treatment). Patterned bars represent cases with a minimum 50% reduction in CA 19-9 levels from baseline, with a CA 19-9 value >10,000 at baseline. # denotes instances where CA 19-9 value at baseline or month 2 were unavailable.
Figure 11:
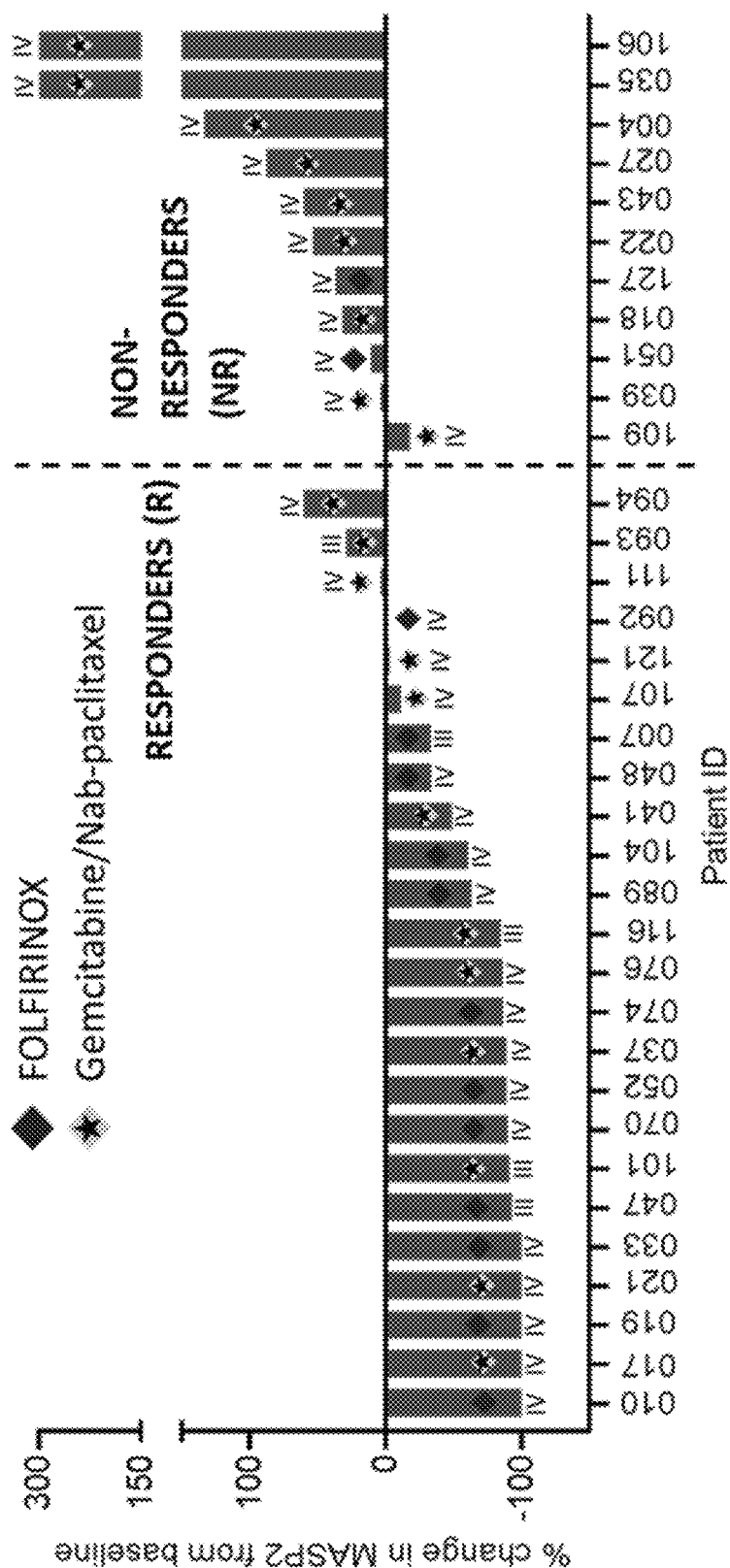
FIG. 11—Waterfall plot depicting percentage changes in MASP2 levels in serum EVs in R and NR groups in month 2 (post-treatment) compared to month 0 (pre-treatment). Chemotherapeutic drug (FOLFIRINOX or Gemcitabine/nab-paclitaxel) and pancreatic cancer stage (III or IV) are indicated for each patient.

Next, we aimed to investigate whether EV-MASP2 exhibits distinct expression patterns in the NR patient group. This group, characterized by short-term survival (average OS for the NR group was 4 months vs 16 months for the R group), and inconsistent CA 19-9 levels, poses a unique challenge in treatment response prediction. Contrary to the R group, in the NR patient cohort, we observed a significant rise by at least 20% in serum EV-MASP-2 levels post-treatment in 73% of the NR patients (FIGS. 9A&B). This observation is significant, as first, the dynamic patterns of alteration in EV-MASP-2 levels in both the NR group and R groups are concordant with each other. Second, in the NR group, CA 19-9 levels were unable to predict non-responsiveness, where there was a rise in 1 out of 9 patients and exhibited patterns similar to the R group of patients (FIG. 10). In contrast, EV-MASP2 demonstrated the ability to predict non-responsiveness to chemotherapy in the NR group of patients (rise in 8 of 11 patients) and displayed an opposite trend compared to that observed during remission in the R group (FIG. 11). These effects appear to be independent of the chemotherapy regimen utilized.

Collectively, our analysis of advanced pancreatic cancer patient serum indicates EV-derived MASP-2 as a potential biomarker of chemotherapeutic responsiveness or cancer remission, particularly for pancreatic cancer. Declining levels of EV-MASP-2 correlate with pancreatic cancer treatment response, whereas increasing levels of EV-MASP-2 post-treatment predict chemo non-responsiveness. In contrast, in our cohort of NR patients, CA19-9 failed to rise and often decreased, thus underperforming compared with MASP-2 as a biomarker.

With these observations, we next sought to evaluate the predictive capability and performance of MASP-2 in chemotherapeutic responsiveness and overall patient survival as assessed through various metrics described.

Example 5: Predictive Performance of MASP-2 in Chemotherapeutic

Figure 3:
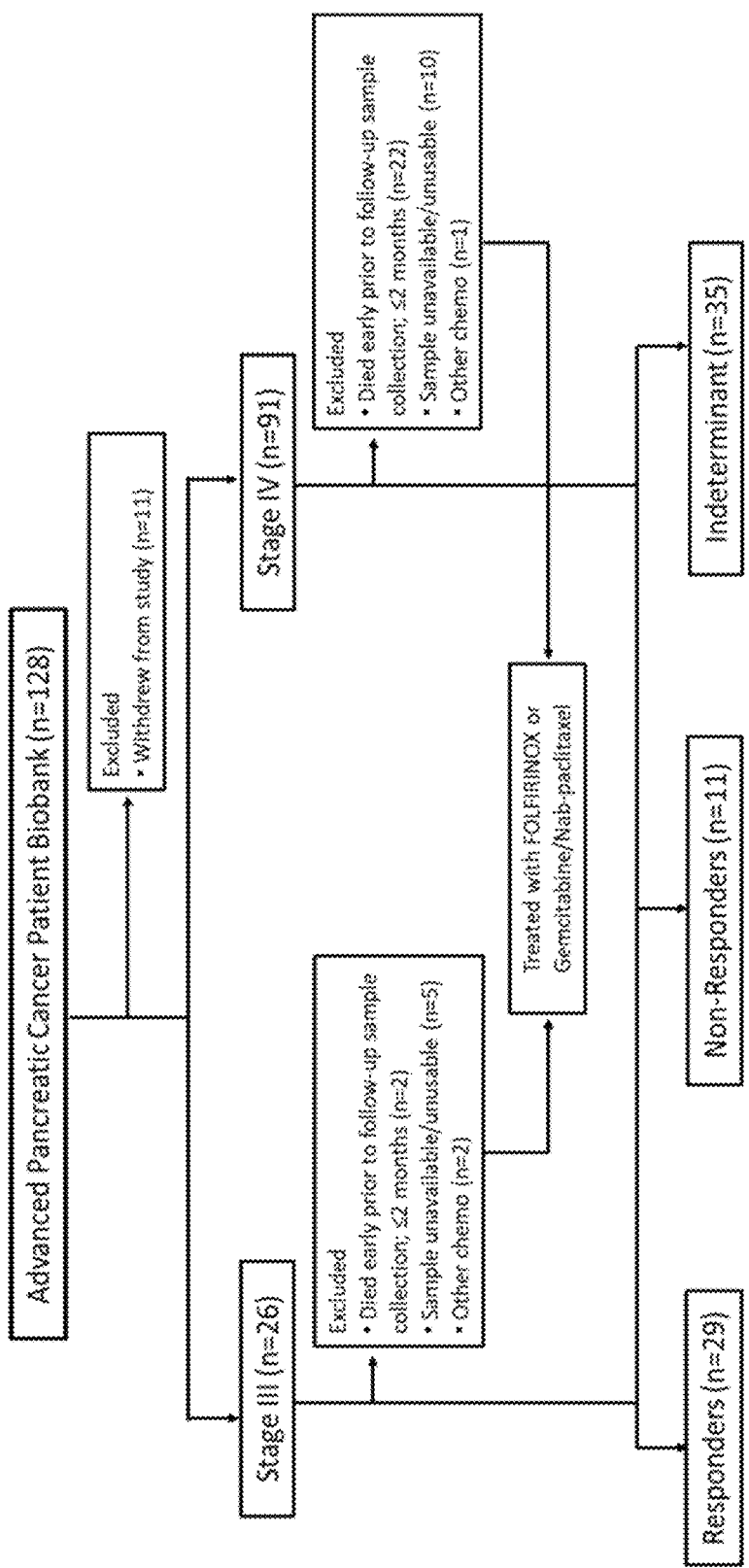
FIG. 3—Consort flowchart for recruited patients in an exemplary study.
Figure 12:
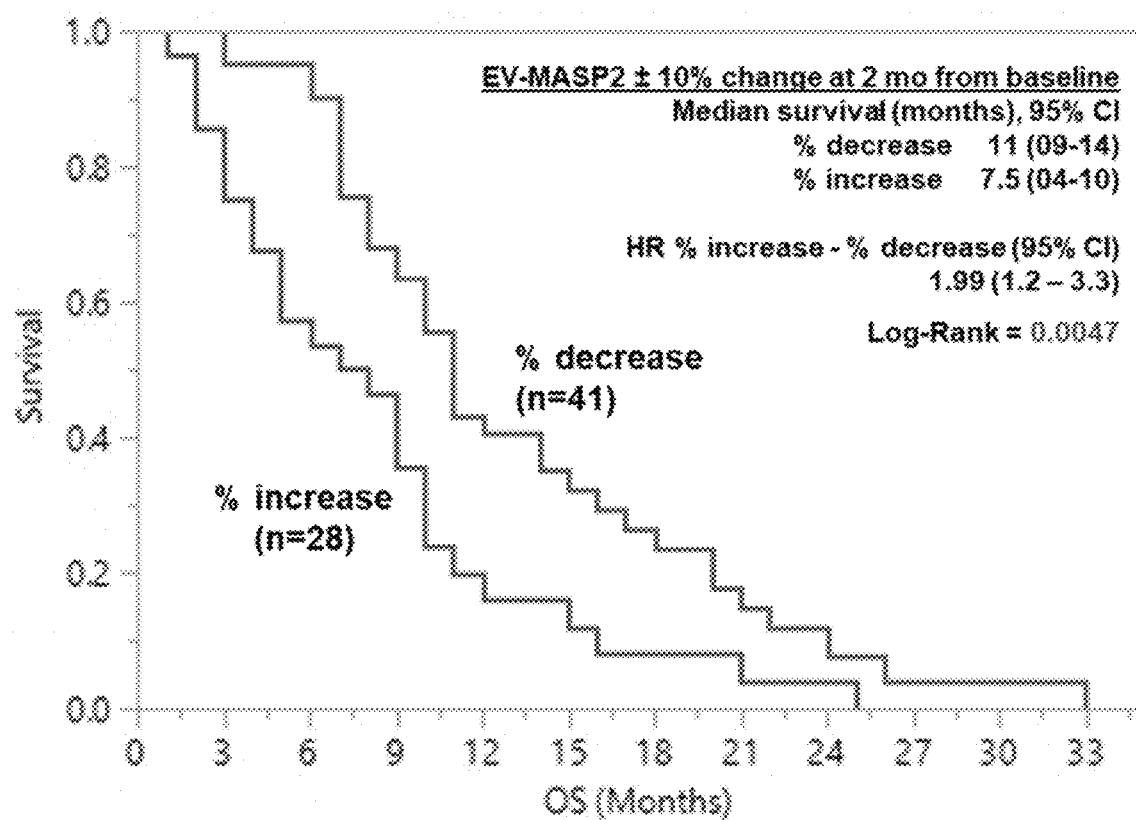
FIG. 12—Kaplan-Meier (K-M) plot for overall survival analysis in PC patients, comparing those with a ≥10% rise (blue) versus those with a ≥10% drop (red) in serum EV-MASP2 levels at month 2 compared to baseline. Median survival times, hazard ratio (HR), and significance from the log-rank test are shown to elucidate the differences in the survival outcomes between the tested groups.
Figure 13A:
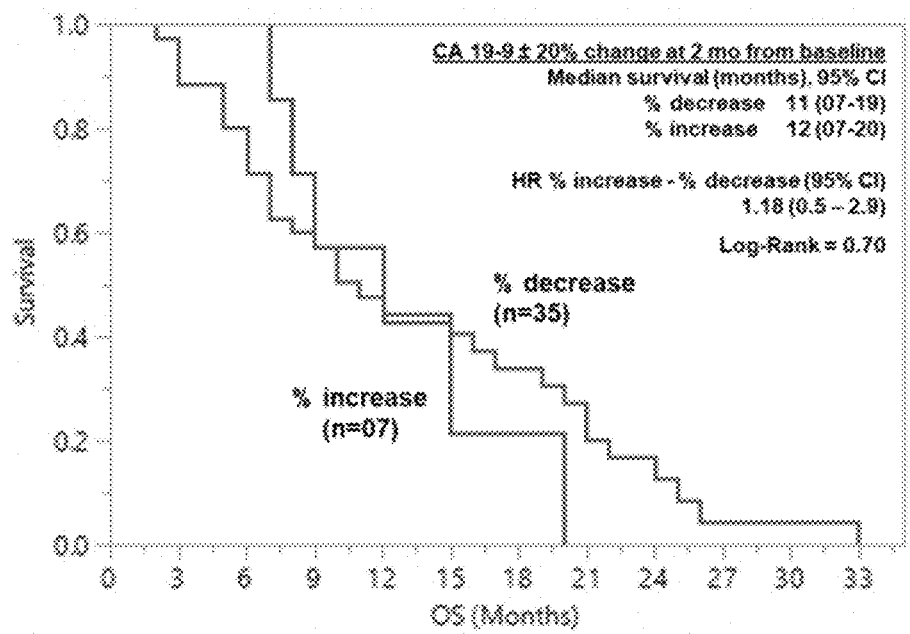
Figure 13B:
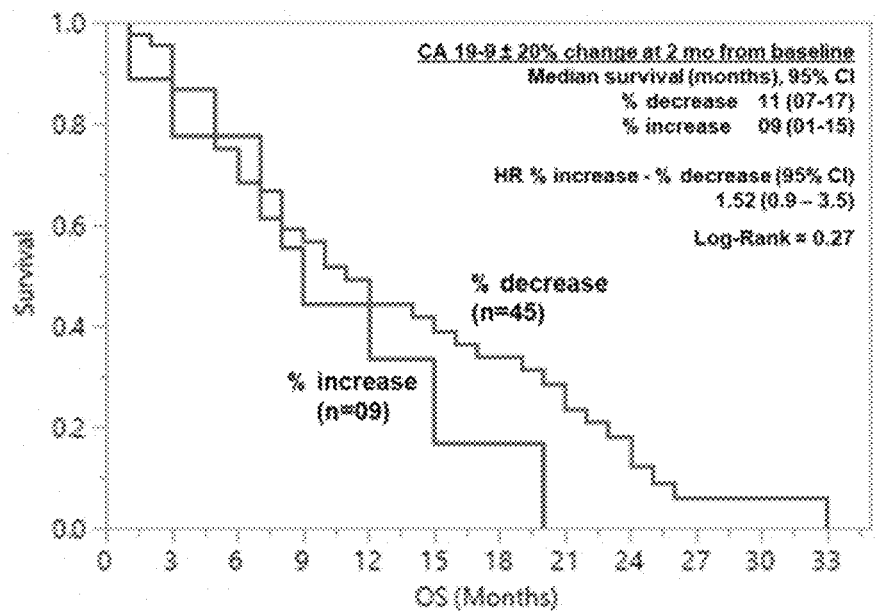

Responsiveness: In our study cohort, as depicted in the consort diagram (FIG. 3), most patients were categorized as having an indeterminate response to treatment as they could not be classified as either R or NR based on changes in CA 19-9 and CT findings. Combining data for EV-MASP-2 levels from these additional 35 patients with the R and NR patient data yielded a larger group (n=75) for assessing the relationship between EV-MASP-2 changes and survival. With this, we found that patients with a ≥10% drop in EV-MASP-2 had a median survival of 11 months (95% CI: 8-14), contrasting with 7.5 months (CI: 4-10; p=0.0047) for those with a ≥10% rise. See FIG. 12. In comparison, changes in CA 19-9 levels in eligible patients within this group (n=42), (excluding those with low or negative CA 19-9 values or high bilirubin, which causes falsely elevated values), did not display prognostic power, exhibiting only a one-month difference in median survival between those with a ≥20% decrease versus increase (FIG. 13A). Notably, CA 19-9's predictive capacity across the entire eligible cohort (n=54), inclusive of those excluded from EV-MASP2 analyses, also failed to reveal significant survival differences with a ≥20% alteration in either direction (FIG. 13B). These observations suggest EV-MASP2 is a better predictor of chemotherapeutic responsiveness and overall survival than CA 19-9 within our study cohort.

Subsequently, we evaluated the efficacy of EV-MASP2 exclusively in patients diagnosed with stage IV metastatic pancreatic cancer. To this end, we categorized EV-MASP2 level changes into several thresholds (+10%, +20%, ±30%, ±50% and ±90%) and assessed its predictive potential at 3, 6, 9, and 12 months after the start of chemotherapy. The analysis incorporated sensitivity, specificity, precision, and the F1 score to evaluate the prognostic significance of these changes for overall survival. Sensitivity quantifies the true positive rate, delineating the proportion of non-survivors correctly identified through elevated EV-MASP2 levels within the designated timeframe (months). Specificity computes the true negative rate, reflecting the proportion of survivors who exhibited a reduction in EV-MASP2 levels beyond the specified timepoint. Precision, or positive predictive value (PPV), represents the ratio of true positive predictions to the total number of positive predictions. Elevated precision indicates that prognostications of non-survival predicated on EV-MASP2 level increments are likely accurate. And finally, the F1 score is a composite metric synthesizing precision and sensitivity to provide harmony between the true positive rate and the precision of the prognostic model.

EV-MASP2 at 30% Threshold (n=42): At 6 months, the sensitivity was 100%, specificity 68.75%, precision 50.00%, and F1 score 66.67%. At 9 months, improvements were observed with sensitivity at 72.22%, specificity 70.83%, precision 65.00%, and F5 score 68.42%. By 12 months, the sensitivity slightly decreased to 62.96%, but specificity (78.57%), precision (85.00%), and F1 score (72.34%) showed significant improvements over 10% and 20% thresholds, indicating enhanced predictive accuracy over time (Table 3).

EV-MASP2 at 50% Threshold (n=33): At 6 months, the model demonstrated a 100% sensitivity, 65.38% specificity, 43.75% precision, and 60.87% F1 score. The 9-month data showed a balance between sensitivity (64.29%) and precision (56.25%), resulting in a 60.00% F5 score. At 12 months, the predictive model further refined its accuracy with a sensitivity of 56.52%, specificity of 66.67%, precision of 81.25%, and an F1 score of 66.67% (Table 3).

EV-MASP-2 at 90% Threshold (n=15): Although a smaller sample size, this threshold demonstrated a unique pattern, starting with 100% sensitivity and 63.64% specificity at 6 months, precision was 50.00%, and F1 score 66.67%. At 9 months, the sensitivity remained high at 100%, with specificity at 70.00%, precision at 62.50%, and F1 score at 76.92%. By 12 months, the model showed improvements in overall metrics: sensitivity at 77.78%, specificity at 80.00%, precision at 87.50%, and the highest F1 score among all thresholds at 82.35% (Table 3, below).

TABLE 3

Predictive values of serum EV MASP2 level changes for survival in stage IV PC patients treated with chemotherapy.

| MASP2 Threshold | Overall survival (months) | Sensitivity | Specificity | Precision | F1 Score |
| --- | --- | --- | --- | --- | --- |
| ±10% (n = 54) | 6 | 91.67% | 71.43% | 47.83% | 62.86% |
| | 9 | 63.64% | 71.88% | 60.87% | 62.22% |
| | 12 | 55.56% | 83.33% | 86.36% | 67.81% |
| ±20% (n = 47) | 6 | 100% | 67.57% | 45.45% | 62.50% |
| | 9 | 72.22% | 68.97% | 59.09% | 65.00% |
| | 12 | 62.07% | 81.25% | 85.71% | 72.00% |
| ±30% (n = 42) | 6 | 100% | 68.75% | 50.00% | 66.67% |
| | 9 | 72.22% | 70.83% | 65.00% | 68.42% |
| | 12 | 62.96% | 78.57% | 85.00% | 72.34% |
| ±50% (n = 33) | 6 | 100% | 65.38% | 43.75% | 60.87% |
| | 9 | 64.29% | 63.16% | 56.25% | 60.00% |
| | 12 | 56.52% | 66.67% | 81.25% | 66.67% |
| ±90% (n = 15) | 6 | 100% | 63.64% | 50.00% | 66.67% |
| | 9 | 100% | 70.00% | 62.50% | 76.92% |
| | 12 | 77.78% | 80.00% | 87.50% | 82.35% |

Altogether, these data, across different levels of change for EV-MASP2, demonstrate its potential as a prognostic marker for overall survival. The increasing specificity, precision, and F1 scores over time, especially at the 12-month interval, highlight the utility of EV-MASP2 level changes in predicting long-term patient outcomes. These findings suggest that EV-MASP2 level monitoring could be integrated into clinical practice for risk stratification and management of patients, potentially guiding therapeutic interventions and improving patient care.

Figure 14:
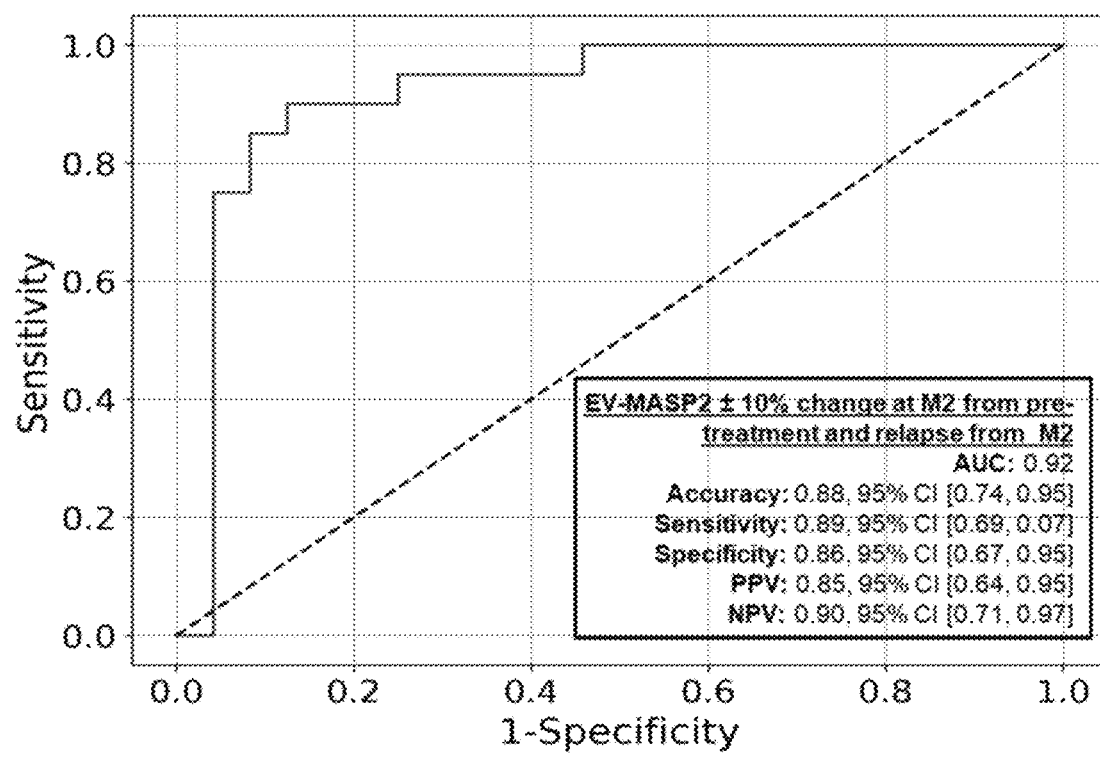
FIG. 14—ROC curve analysis showing the performance of MASP2 in predicting chemotherapeutic responsiveness. The model evaluates greater than and less than 10% changes in serum EV-MASP2, comparing these changes at month 2 (M2) from pre-treatment, and at relapse from M2. Performance metrices such as accuracy, sensitivity, specificity, positive predictive value (PPV) and negative predictive value (NPV) are indicated for the tested model.

To further validate our findings, an ROC curve analysis was conducted to assess the performance of early EV-MASP2 changes (M2) with a threshold of ±10% in predicting chemotherapeutic response in the R patient cohort (n=24). Data pre-processing was performed by importing the dataset into a pandas DataFrame (Python), ensuring the integrity of our analysis utilizing pandas' "dropna" function. For compatibility with the confusion matrix analysis, the 'Observed' variables (percent changes of EV-MASP2 at M2 compared to pre-treatment as well as relapse timepoints) were transformed to a binary format. To normalize the data scales, z-scores were calculated for the 'PercentChange' variable using the zscore function from SciPy's stats module. Using the scikit learn module, the components of the confusion matrix were calculated for the computation of key metrics, including True Negatives (TN), False Positives (FP), False Negatives (FN), and True Positives (TP). These components were instrumental in deriving the accuracy, sensitivity (true positive rate), specificity (true negative rate), positive predictive value (PPV), and negative predictive value (NPV) of the model. To estimate the uncertainty associated with each metric, we calculated 95% confidence intervals using the Wilson score interval method, facilitated by the statsmodels.stats.proportion module. This approach provided a statistical measure of the reliability of the calculated metrics, enhancing the interpretability of the model's predictive performance (FIG. 14).

The ROC curve analysis yielded an AUC of 0.92, reflective of an excellent model performance of serum EV-MASP-2 in effectively distinguishing between disease progression towards remission and relapse in advanced pancreatic cancer patients. A high sensitivity (true positive rate) of 0.89 indicates the effectiveness of EV-MASP2 changes in identifying occurrence of relapse in the course of the treatment and disease progression, while a specificity (true negative rate) of 0.86 implies that the changes in EV-MASP2 can accurately identify patients progressing toward remission. The model demonstrated an accuracy of 0.88 with a 95% CI [0.74, 0.95], reflective of the overall correctness of the test both when it predicts relapse and when it predicts remission. Finally, PPV and NPV values of 0.85 and 0.90 further corroborate the above bolstering the reliability of the predictive performance of EV-MASP-2 changes in assessing disease progression towards true relapse and true remission respectively (FIG. 14).

Figure 15:
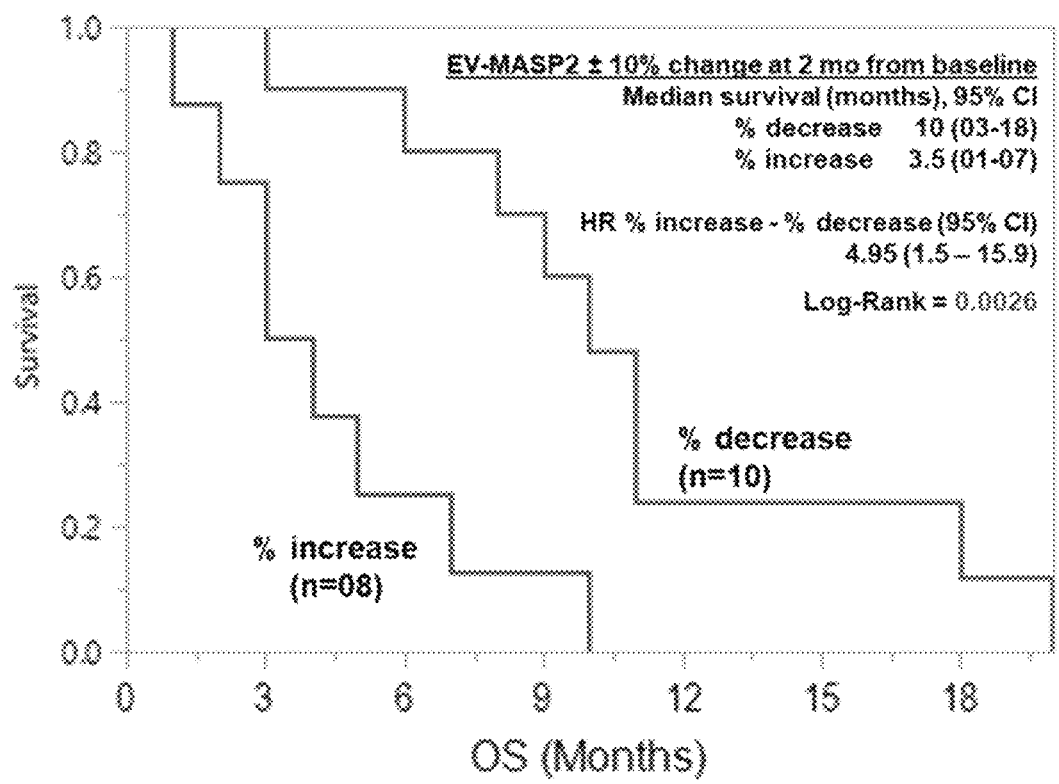

Building on our investigation, we next explored the use of EV-MASP2 levels in situations where CA 19-9 is unevaluatable, such as those who present with hyperbilirubinemia from obstructive jaundice, a situation in which CA 19-9 is spuriously elevated. We identified 18 patients who had bilirubin levels exceeding 1.3 (upper limit of normal) at presentation and a follow-up biobanked serum sample. In these patients, a 10% decline compared to a 10% rise in EV-MASP2 predicted for survivals of 10 months vs. 3.5 months, respectively (FIG. 15). This observation holds significant clinical relevance, suggesting that analysis of serum EV-MASP2 may have prognostic utility in situations where CA 19-9 cannot be utilized for this purpose. Particularly, this finding suggests that EV-MASP2 should be used instead of CA 19-9 in cases of hyperbilirubinemia because CA 19-9 is falsely elevated in hyperbilirubinemia.

The collective findings highlight the significance of EV-MASP-2 as an early prognostic indicator for assessing chemotherapeutic response and overall survival in pancreatic cancer patients. The suite of predictive metrics related to the alterations in EV-MASP-2 levels elucidates its efficacy in stratifying patients according to their risk of experiencing adverse or favorable outcomes subsequent to initial chemotherapy regimens. Importantly, insights into the mechanistic implications of EV-MASP-2 directional alterations can facilitate refined clinical decision-making processes, enabling personalized treatment strategies and optimized patient management in the context of pancreatic cancer care.

Example 6: Plasma MASP-2

While it was discovered the EV-MASP-2 levels are more sensitive, ws-MASP-2 measured from whole serum (ws) rather than EVs was investigated. To compare changes in MASP-2 levels, both EV-MASP-2 and ws-MASP-2 in patients categorized as responders (R) and non-responders (NR) were measured. Serum was diluted at 1:800 dilution following manufacturer's protocol. Subsequently, 50 μl of the diluted serum was loaded onto the plate with primary antibody at 1:1 ratio in replicates and MASP2-ELISA was performed following manufacturer's guidelines (ab278121, Abcam).

Figure 16A:
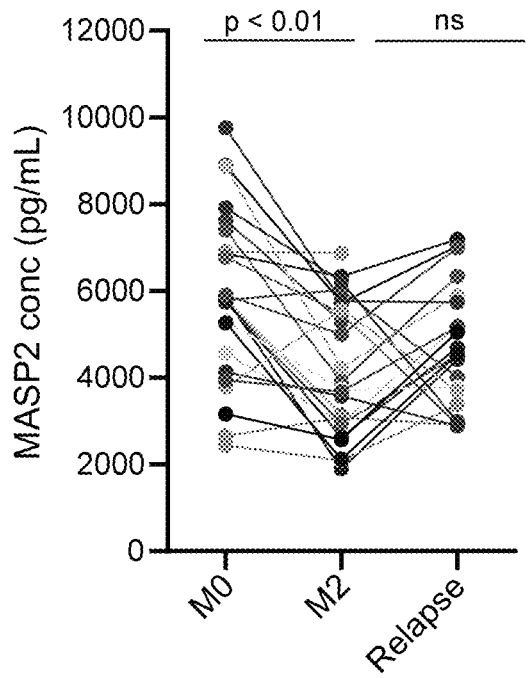
FIGS. 16A and 16B—Whole serum MASP2 levels measured by ELISA in R and NR patient groups. (16A) Changes in serum MASP2 concentrations (pg/mL) of the R patient group (n=24) tracked across pre-treatment (M0), remission, and relapse timepoints. (16B) Changes in serum MASP2 concentrations (pg/mL) of the NR patient group (n=11) at pre- and post-treatment timepoints.

In the serum samples, a significant decrease in ws-MASP-2 levels at month 2 compared to baseline was observed, with reductions exceeding 10% and 20% in 75% and 62% of the R group, respectively (FIG. 16A). Additionally, when analyzing ws-MASP-2 levels from month 2 to relapse, 62% of the R patients who experienced disease relapse exhibited at least a 10% increase in ws-MASP-2 levels (52% showed at least a 20% increase). While there was significance for the decrease in ws-MASP-2 at month 2 compared to pre-treatment (p<0.01), no significance was observed for the change from month 2 to relapse.

Figure 16B:
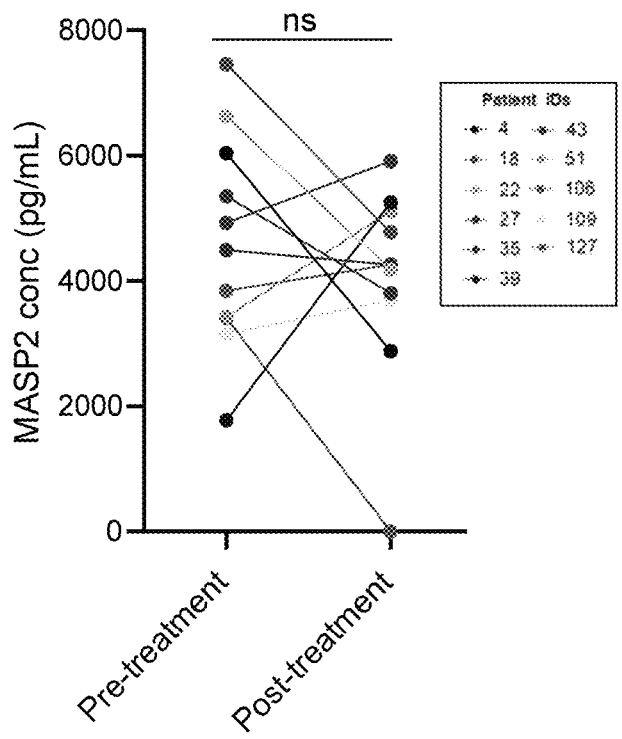
Figure 17A:
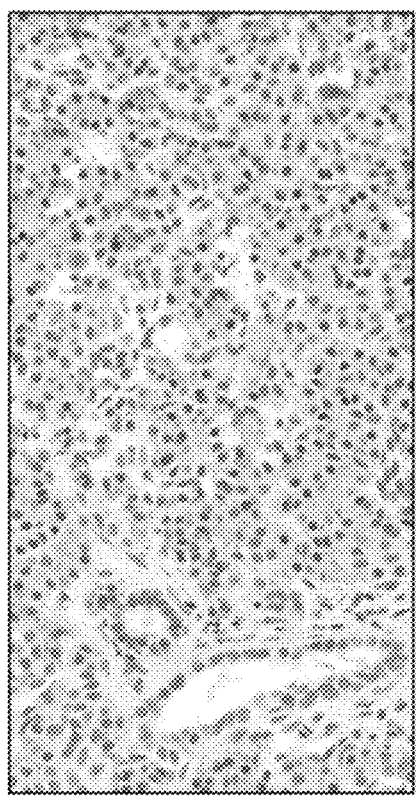
FIGS. 17A-17D Immunohistochemical staining of MASP2 in primary and liver metastatic human PDAC compared to normal tissues. (17A) Normal pancreas where predominant staining is seen in acinar cells. (17B) Normal liver tissue with maximal and intense MASP2 immunoreactivity in the hepatocytes, consistent with expected expression patterns of the protein. (17C) Advanced stage primary PDAC (pancreas) tissue acquired by patient biopsy, displaying sparse and heterogenous MASP2 expression within tumor and adjacent stromal compartments; positively stained tumor cells are indicated by black arrows. (17D) Metastatic PDAC within liver biopsy specimen showcasing enhanced MASP2 expression predominantly within stromal regions, while a subset of tumor cells (indicated by black arrows) also displays positive staining, with an overall more extensive expression profile compared to primary PDAC tissue.
Figure 17B:
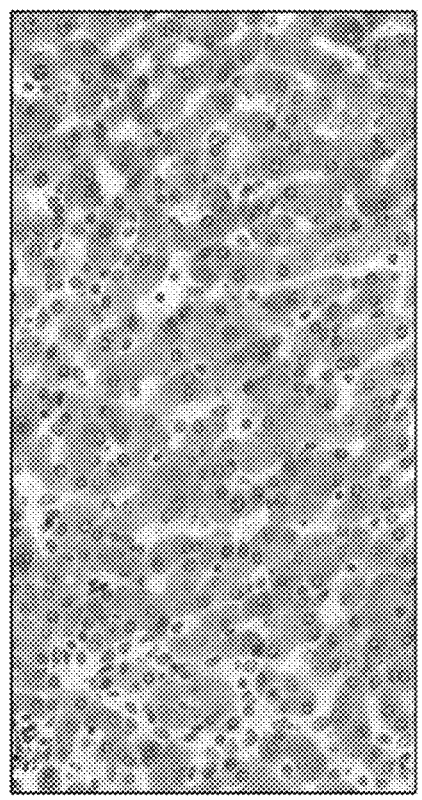
Figure 17C:
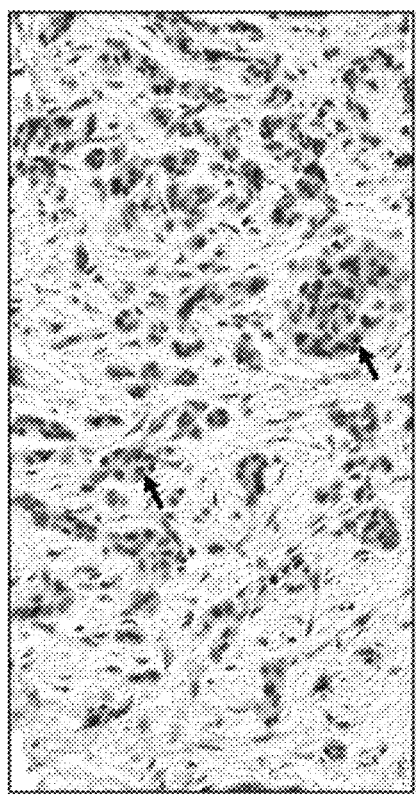
Figure 17D:
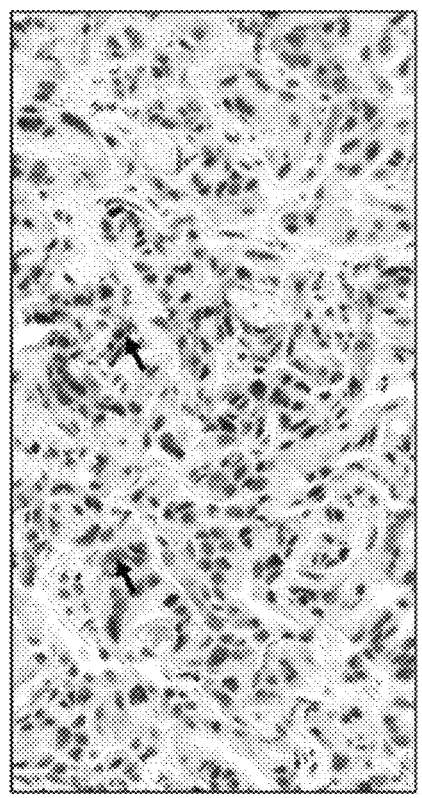

In contrast, among the NR group (n=11), no discernible correlation was found between pre- and post-treatment changes in ws-MASP-2 levels within serum samples. Specifically, 36% of patients showed at least a 10% increase, while 45% showed at least a 10% decrease (FIG. 16B). In conjunction with the foregoing EV-MASP-2 results, it can be concluded that EV-MASP-2 has superior reliability and specificity compared to ws-MASP-2. Still, these results for ws-MASP-2 are promising and support that measurement of MASP-2 from biological samples other than EV-MASP-2 have predictive power.

Example 7: Immunohistochemistry (IHC)

Building upon the preliminary observations of MASP-2 within serum EVs of advanced pancreatic cancer patient cohorts, and its integral role in the complement pathway, our investigation aimed to uncover the potential origin and mechanistic significance of MASP-2 in pancreatic cancer pathogenesis. To this end and given the high incidence of liver metastasis (60%) within our patient cohort at the point of PC diagnosis, we evaluated the expression patterns of MASP-2 by IHC analysis across primary and metastatic pancreatic ductal adenocarcinoma (PDAC) microenvironments from advanced pancreatic cancer patient biopsies and made comparisons with normal pancreas and liver specimens.

Archived human pancreatic cancer biopsy specimens from deceased patients were obtained from the Danbury Hospital and Norwalk Hospital departments of pathology after obtaining approval for an investigator-initiated study from the BRANY Institutional Review Board. Primary pancreatic tumor or metastatic liver sites were prepared in formalin-fixed and paraffin-embedded tissues. 4 μm sections were cut from the tissue blocks and mounted on silane-coated glass slides. Tissue sections were deparaffinized, rehydrated and incubated with 3% hydrogen peroxide in methanol for 15 mins to quench endogenous peroxidase activity. Antigen retrieval was carried out by heating at 95° C. for 20 mins in an antigen retrieval buffer (AR9640, Leica). Non-specific antibody binding was blocked by incubation with Novolink Protein Block (RE7280-CE, Leica) for 30 mins. The slides were then incubated with primary antibody against MASP-2 (ab277520, abcam) at 1:200 for 30 mins at room temperature, followed by anti-rabbit poly-HRP-IgG secondary antibody (PV6118, Leica) for 20 mins at room temperature. Visualization was carried out using 3,3'-diaminobenzidine (DAB) for 10 mins and counterstaining with hematoxylin for 3 mins. The slides were intensively examined by three independent pathologists at Nuvance Health for quality control and evaluation of percentage of tumor, fibrosis, normal or normal adjacent tissues Each sample received a score determined by the staining intensity: 0 for no staining or very weak, 1 for weak, 2 for moderate, and 3 for strong. "High" MASP-2 expression was designated for a score of ≥2, while "low" expression was assigned to a score within the range of 0-1. Computer-assisted morphometric analysis of the digital images was performed using the FDA approved positive pixel algorithm for quantification of MASP-2 positivity in the tissue specimens.

MASP-2, a serum protease predominantly synthesized in the liver, was found to be significantly expressed in normal liver hepatocytes, as evidenced by IHC staining (see FIG. 17). This finding aligns with the expected liver production of MASP2. In contrast, its expression in normal pancreatic tissue appeared nominal, with only a moderate presence in acinar cells. Our analysis of the tumor biopsies revealed minimal MASP2 staining in tumor cells within primary PDAC tissues, with mild staining in the infiltrating immune cells. Liver metastatic PDAC sites exhibited comparatively higher MASP-2 expressions, particularly highlighted by moderate staining within the tumor stroma and among the infiltrating immune cells (FIG. 17).

This observed pattern of differential expression, especially in the context of metastatic liver sites, suggests a possible mechanistic role of MASP-2 in tumor progression. The stromal and immune cell associated MASP-2 expression in metastatic site hints at a complex interplay, suggesting a role of MASP-2 in tumor microenvironment remodeling and immune evasion mechanisms associated with metastatic progression.

The interplay between the complement system and macrophage polarization significantly influences pancreatic cancer angiogenesis, progression, and metastasis. M1-polarized macrophages, classically activated, are instrumental in early pancreatic lesion development, driving Th1 responses and emitting pro-inflammatory cytokines. Conversely, M2-polarized macrophages, associated with tissue remodeling and desmoplastic stroma, dominate tumor-associated macrophages (TAMs), thereby facilitating metastasis and chemoresistance. The regulation of M2 macrophages by complement components, including anaphylatoxins (C3a and C5a) which are downstream of MASP-2-mediated C3 and C5 activation, suggests a role of MASP-2 in modulating pancreatic cancer pathogenesis and treatment response.

The observations herein propose MASP-2 not only as a reliable biomarker for pancreatic cancer and potentially other cancer progression, but also as a promising therapeutic target. Its involvement in the complement pathway and differential expression across pancreatic cancer stages lay the groundwork for a compelling narrative where mechanistic roles of MASP-2 could be leveraged for therapeutic intervention. Targeting MASP-2 inhibition could offer a dual benefit: modulating the complement pathway by hindering tumor-promoting M2-polarization to reinstate immunosurveillance and disrupting tumor-stromal interactions that underpin metastatic dissemination. Reduced MASP-2 levels in systemic EVs, correlating with chemotherapy responsiveness, may thus represent a strategic point of intervention to counteract pancreatic cancer progression.

Incorporation by Reference

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

Equivalents

The invention can be embodied in other specific forms without departing from the spirit or essential characteristics thereof. The foregoing embodiments are to be considered in all respects illustrative rather than limiting on the invention described herein. In the various embodiments of the compositions and methods of the present invention, where the term comprises is used with respect to the recited components of the compositions or steps of the methods, it is also contemplated that the compositions and methods consist essentially of, or consist of, the recited steps or components. Furthermore, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into additional materials.

All percentages and ratios used herein, unless otherwise indicated, are by weight.

What is claimed is:

1. A method for determining whether to continue or discontinue a first-line cancer therapy in a pancreatic cancer patient in need thereof, the method comprising the steps of:
    (a) obtaining a blood sample from the patient prior to or at commencement of a first-line cancer therapy;
    (b) isolating extracellular vesicles from the blood sample and determining, from the isolated extracellular vesicles, a baseline extracellular vesicle-derived mannan-binding protein-associated serine protease-2 (EV-MASP-2) level for the patient,
    (c) administering the first-line cancer therapy to the patient according to a treatment regimen over a treatment time period,
    (d) obtaining a blood sample from the patient during the treatment time period;
    (e) isolating extracellular vesicles from the blood sample obtained during the treatment time period and determining, from the isolated extracellular vesicles, a treatment EV-MASP-2 level;
    (f) determining whether the treatment EV-MASP-2 level has decreased relative to the baseline EV-MASP-2 level; and
    (g-i) continuing administering the first-line cancer therapy according to the treatment regimen if the treatment EV-MASP-2 level has decreased relative to the baseline EV-MASP-2 level, or
    (g-ii) discontinuing administering the first-line cancer therapy according to the treatment regimen if the treatment EV-MASP-2 level has not decreased relative to the baseline EV-MASP-2 level.

2. The method of claim 1, wherein discontinuing administering the first-line cancer therapy according to the treatment regimen comprises:
    (g-ii-a) commencing administering the first-line cancer therapy according to a different treatment regimen; or
    (g-ii-b) discontinuing administering the first-line cancer therapy and administering no further cancer therapy; and/or
    (g-ii-c) commencing administering of second-line cancer therapy according to a treatment regimen.

3. The method of claim 1, wherein the pancreatic cancer is advanced pancreatic cancer.

4. The method of claim 3, wherein the advanced pancreatic cancer is stage III or stage IV pancreatic cancer.

5. The method of claim 1, wherein the first-line cancer therapy is one or more of chemotherapy, biological therapy, immunotherapy, and hormonal therapy.

6. The method of claim 1, wherein the first-line cancer therapy is 5-fluorouracil, FOLFIRINOX, or gemcitabine alone or in combination with nab-paclitaxel, capecitabine, cisplatin, and/or oxaliplatin.

7. The method of claim 1, wherein the blood sample of step (d) is collected during the treatment time period at a time point from about 2 weeks to about 4 months after commencement of the first-line cancer therapy to determine the treatment EV-MASP-2 level.

8. The method of claim 7, wherein the time point is about 2 months after commencement of the first-line cancer therapy.

9. The method of claim 1, wherein the first-line cancer therapy is administered at a first dosage and then, if the EV-MASP-2 level has not decreased relative to the baseline EV-MASP-2 level, the first-line cancer treatment is administered at a higher, second dosage.

10. The method of claim 1, comprising:
    continuing administering the first-line cancer therapy according to the treatment regimen in step (g-i), or
    commencing administering a second-line cancer therapy according to a treatment regimen in step (g-ii).

11. A method for determining whether to continue or discontinue a first-line cancer therapy in a pancreatic cancer patient in need thereof, the method comprising the steps of:
    (a) obtaining a blood sample from the patient prior to or at commencement of a first-line cancer therapy;
    (b) isolating extracellular vesicles from the blood sample and determining, from the isolated extracellular vesicles, a baseline extracellular vesicle-derived mannan-binding protein-associated serine protease-2 (EV-MASP-2) level for the patient,
    (c) administering the first-line cancer therapy to the patient according to a treatment regimen over a treatment time period,
    (d) obtaining a blood sample from the patient during the treatment time period;
    (e) isolating extracellular vesicles from the blood sample obtained during the treatment time period and determining, from the isolated extracellular vesicles, a treatment EV-MASP-2 level;
    (f) comparing the treatment EV-MASP-2 level to the baseline EV-MASP-2 level; and
    (g-i) continuing administering the first-line cancer therapy according to the treatment regimen if the treatment EV-MASP-2 level has decreased from the baseline EV-MASP-2 level by 10% or greater; or
    (g-ii) discontinuing administering the first-line cancer therapy according to the treatment regimen if the treatment EV-MASP-2 level has not decreased from the baseline EV-MASP-2 level, or if the treatment EV-MASP-2 level has decreased from the baseline EV-MASP-2 level by less than 10%.

12. The method of claim 11, wherein discontinuing administering the first-line cancer therapy according to the treatment regimen comprises:
    (g-ii-a) commencing administering the first-line cancer therapy according to a different treatment regimen; or
    (g-ii-b) discontinuing administering the first-line cancer therapy and administering no further cancer therapy; and/or
    (g-ii-c) commencing administering of second-line cancer therapy according to a treatment regimen.

13. The method of claim 11, wherein the pancreatic cancer is advanced pancreatic cancer.

14. The method of claim 13, wherein the advanced pancreatic cancer is stage III or stage IV pancreatic cancer.

15. The method of claim 11, wherein the first-line cancer therapy is one or more of chemotherapy, biological therapy, immunotherapy, and hormonal therapy.

16. The method of claim 11, wherein the first-line cancer therapy is 5-fluorouracil, FOLFIRINOX, or gemcitabine alone or in combination with nab-paclitaxel, capecitabine, cisplatin, and/or oxaliplatin.

17. The method of claim 11, wherein the blood sample of step (d) is collected during the treatment time period at a time point from about 2 weeks to about 4 months after commencement of the first-line cancer therapy to determine the treatment EV-MASP-2 level.

18. The method of claim 17, wherein the time point is about 2 months after commencement of the first-line cancer therapy.

19. The method of claim 11, wherein the first-line cancer therapy is administered at a first dosage and then, if the treatment EV-MASP-2 level has not decreased from the baseline EV-MASP-2 level, or if the treatment EV-MASP-2 level has decreased from the baseline EV-MASP-2 level by less than 10%, the first-line cancer treatment is administered at a higher, second dosage.

20. The method of claim 11, comprising:
continuing administering the first-line cancer therapy according to the treatment regimen in step (g-i), or
commencing administering a second-line cancer therapy according to a treatment regimen in step (g-ii).

* * * * *